US009334529B2

(12) United States Patent
Leijon et al.

(10) Patent No.: US 9,334,529 B2

(45) Date of Patent: May 10, 2016

(54) GENOTYPING OF N LOCI IN A TARGET NUCLEIC ACID MOLECULE

(75) Inventors: Mikael Leijon, Kungsängen (SE); Sándor Belák, Uppsala (SE)

(73) Assignee: Leijon diagnostics AB, Södertälje (SE)

( * ) Notice: Subject to any disclaimer, the term of this patent is extended or adjusted under 35 U.S.C. 154(b) by 911 days.

(21) Appl. No.: 13/505,694

(22) PCT Filed: Nov. 3, 2010

(86) PCT No.: PCT/SE2010/051200

§ 371 (c)(1), (2), (4) Date: May 2, 2012

(87) PCT Pub. No.: WO2011/056133

PCT Pub. Date: May 12, 2011

(65) Prior Publication Data

US 2012/0219954 A1 Aug. 30, 2012

(30) Foreign Application Priority Data

Nov. 3, 2009 (SE) ...................................... 0950824

(51) Int. Cl.

*C12P 19/34* (2006.01)
*C12Q 1/68* (2006.01)

(52) U.S. Cl.

CPC ............ *C12Q 1/6827* (2013.01); *C12Q 1/6858* (2013.01)

(58) Field of Classification Search

USPC ............................................... 435/6.12, 91.2

See application file for complete search history.

(56) References Cited

U.S. PATENT DOCUMENTS

| | | | | |
|---|---|---|---|---|
| 2003/0096277 | A1 | 5/2003 | Chen | |
| 2003/0130497 | A1 | 7/2003 | Bai et al. | |
| 2003/0211489 | A1 | 11/2003 | Shen et al. | |
| 2005/0214825 | A1 | 9/2005 | Stuelpnagel | |
| 2010/0120038 | A1* | 5/2010 | Mir et al. | 435/6 |
| 2012/0258447 | A1* | 10/2012 | Chun | 435/5 |

FOREIGN PATENT DOCUMENTS

| | | | |
|---|---|---|---|
| WO | WO-2004/099439 | | 1/2004 |
| WO | WO-2006/023919 | | 3/2006 |
| WO | WO 2009/004335 | A1 | 1/2009 |
| WO | WO 2009/126678 | A2 | 10/2009 |

OTHER PUBLICATIONS

Bao, Y. et al. (2008) "The Influenza Virus Resource at the National Center for Biotechnology Information," Journal of Virology 82(2):596-601.

Belák, S. et al. (2009) "New developments in the diagnosis of avian influenza," Rev. sci. tech. Off. Int. Epiz. 28(1):233-243.

Broude, N.E. et al. (2001) "Multiplex allele-specific target amplification based on PCR suppression," PNAS 98(1):206-211.

Chamberlain, J.S. et al. (1988) "Deletion screening of the Duchenne muscular dystrophy locus via multiplex DNA amplification," Nucleic Acids Research 16(23):11141-11156.

Clamp, M. et al. (2004) "The Jalview Java alignment editor," Bioinformatics 20(3):426-427.

Edgar, R.C. (2004) "Muscle: multiple sequence alignment with high accuracy and high throughput," Nucleic Acids Research 32(5):1792-1797.

Gall, A. et al. (2008) "Universal Primer Set for Amplification and Sequencing of $HA_0$ Cleavage Sites of All Influenza A Viruses," Journal of Clinical Microbiology 46(8):2561-2567.

Gall, A. et al. (2009) "Design and Validation of a Microarray for Detection, Hemagglutinin Subtyping, and Pathotyping of Avian Influenza Viruses," Journal of Clinical Microbiology 47(2):327-334.

Han, J. et al. (2006) "Simultaneous Amplification and Identification of 25 Human Papillomavirus Types with Templex Technology," Journal of Clinical Microbiology 44(11):4157-4162.

Hardenbol, P. et al. (2003) "Multiplexed genotyping with sequence-tagged molecular inversion probes," Nature Biotechnology 21(6):673-678.

Heine, H.G. et al. (2007) "Rapid Detection of Highly Pathogenic Avian Influenza H5N1 Virus by TaqMan Reverse Transcriptase-Polymerase Chain Reaction," Avian Diseases 51:370-372.

Hoffmann, B. et al. (2007) "Rapid and Highly Sensitive Pathotyping of Avian Influenza A H5N1 Virus by Using Real-Time Reverse Transcription-PCR," Journal of Clinical Microbiology 45(2):600-603.

Klenk, H-D. et al. (1994) Chapter 14: "Activation Cleavage of Viral Spike Proteins by Host Proteases," Cellular Receptors for Animal Viruses:241-281.

Pemov, A. et al. (2005) "DNA analysis with multiplex microarray-enhanced PCR," Nucleic Acids Research 33(2):1-9.

Rychlik, W. et al. (1990) "Optimization of the annealing temperature for DNA amplification in vitro," Nucleic Acids Research 18(21):6409-6412.

(Continued)

*Primary Examiner* — Kenneth Horlick

(74) *Attorney, Agent, or Firm* — Foley & Lardner LLP; Antoinette F. Konski

(57) ABSTRACT

The object of the present invention is to provide a novel method that addresses the problem of differentiating large sets of genomic sequences. The invention relates to a method for genotyping N loci present in a sample in a target nucleic acid molecule, wherein each locus is located in a genotype marker region of the nucleic acid molecule, and corresponds to two or more genotypes. Furthermore the invention relates to a kit for performing said method for genotyping. Also the invention relates to a method for designing and producing selection primers, as well as a method for producing detection primers, all of said primers to be used in the method for genotyping or in the kit for performing the genotyping method. The invention further relates to selection primers adapted for genotyping of loci in a target nucleic acid molecule and a computer program product for designing selection primers.

18 Claims, 10 Drawing Sheets

(56) References Cited

OTHER PUBLICATIONS

Schouten, J.P. et al. (2002) "Relative quantification of 40 nucleic acid sequences by multiplex ligation-dependent probe amplification," Nucleic Acids Research 30(12):1-13.
Sherrill, C.B. et al. (2004) "Nucleic Acid Analysis Using an Expanded Genetic Alphabet to Quench Fluorescence," J. Am. Chem. Soc. 126:4550-4556.
Shortreed, M.R. et al. (2005) "A thermodynamic approach to designing structure-free combinatorial DNA word sets," Nucleic Acids Research 33(15):4965-4977.
Shuber, A.P. et al. (1995) "A simplified procedure for developing multiplex PCRs," Genome Research 5:488-493.
Siebert, P.D. et al. (1995) "An improved PCR method for walking in uncloned genomic DNA," Nucleic Acids Research 23(6):1087-1088.
Slomka, M.J. et al. (2007) "Identification of Sensitive and Specific Avian Influenza Polymerase Chain Reaction Methods Through Blind Ring Trials Organized in the European Union," Avian Diseases 51:227-234.
Steinhauer, D.A. (1999) "Role of Hemagglutinin Cleavage for the Pathogenicity of Influenza Virus," Virology 258:1-20.
Varley, K.E. et al. (2008) "Nested Patch PCR enables highly multiplexed mutation discovery in candidate genes," Genome Research 18:1844-1850.
Yacoub, A. et al. (2009) "The rapid molecular subtyping and pathotyping of avian influenza viruses," Journal of Virological Methods 156:157-161.
Zanella, A. et al. (2001) "Avian Influenza Epidemic in Italy Due to Serovar H7N1," Avian Diseases 45:257-261.
Strömqvist Meuzelaar, L. et al. (2007) "MegaPlex PCR: a strategy for multiplex amplification," Nature Methods 4(10):835-837.
Brownie, J. et al. (1997) "The elimination of primer-dimer accumulation in PCR," Nucleic Acids Research 25(16):3235-3241.
Written Opinion of the International Searching Authority (ISA/SE) for International Application No. PCT/SE2010/051200, opinion completed Jan. 26, 2011.
European Search Report of European Patent Application No. EP10828622 dated May 6, 2013.
Hayden et al., "Multiplex-Ready PCR: A new method for multiplexed SSR and SNP genotyping", BMC Genomics, 9(1): 80 (2008).

* cited by examiner

GENOTYPING OF N LOCI IN A TARGET NUCLEIC ACID MOLECULE

CROSS-REFERENCE TO RELATED APPLICATIONS

This application is a national stage application under 35 U.S.C. §371 of International Application No. PCT/SE2010/051200, filed Nov. 3, 2010, which in turn claims priority to Swedish Patent Application No. SE 0950824-3, filed Nov. 3, 2009, the entire contents of each of which are each hereby incorporated by reference into the present disclosure.

FIELD OF THE INVENTION

The invention relates to a method for genotyping one or more loci in a target molecule present in a sample. Furthermore the invention relates to a kit for performing said method. The invention also relates to a method for designing and producing selection primers and a method for producing detection primers, both methods for use in said method for genotyping or in said kit. Also the invention is related to the selection primers as such, as well as to a computer program product that will aid in designing selection primers.

BACKGROUND

In genetic research or in the diagnosis of infectious diseases an important task is the determination and classification of the nucleotide sequences at a particular region of the genome where it falls into two categories, which govern important features of the phenotype. The prime example of such a situation is the cleavage site of the avian influenza virus (AIV) haemagglutinin precursor protein (HA0), which is of a kind characteristic of either a low- or a high-pathogenic virus. The HA0 cleavage sites of the highly pathogenic AIV contain multiple basic amino acid side chains with the minimal motif R/K-X-R/K-R↓G and have so far only been found for H5 and H7 subtypes[1]. In fact, a large number of viruses have been shown to possess surface proteins for which post-translational cleavage is required for activation of infectivity[2], including important pathogens such as human immunodeficiency virus type 1, the filoviruses Ebola and Marburg and flaviviruses, such as the yellow fever virus. Many of these viruses possess cleavage site motifs similar to those of the avian influenza viruses and there are several viruses for which correlations between pathogenicity and cleavage properties have been demonstrated[1,2].

On the basis of the codon representation, the AIV high-pathogenic cleavage site motif can be represented by more than 18,000 distinct sequences at the RNA level. Several hundred of these possible sequences have been discovered in different H5 and H7 subtype viruses and novel viruses with previously unknown cleavage site sequences are constantly emerging. For this reason, attempts to probe the cleavage site in PCR applications have been limited to subsets of influenza viruses[3-6] and current standard procedures for molecular testing of AIV pathogenicity involve nucleotide sequencing of the cleavage site[3,7]. Thus, single tube experiments for AIV pathotyping, able to avoid cumbersome, time consuming and technically demanding nucleotide sequencing, for rapid screening and diagnostic applications, must be able to interrogate the sample in a highly multiplexed way.

A major problem of differentiating large sets of genomic sequences is to devise multiplex amplification methods[8] for obtaining homogeneous amplification of all recognized target segments and to suppress interactions between the primers.

Attempts have been made to suppress interactions betweens primers, e.g. by using the HANDS (Homo-tag Assisted Non-Dimer System) technology, in which chimerical primers (sequence recognizing primers tagged with a universal sequence) are present in relatively low concentration while universal primers targeting the complement of universal tags present on the chimerical primers, which in these scheme effectively brings the amplification to detectable levels, are at higher concentrations[9]. Since the same universal tag sequences extends both the forward and reverse primer of each chimerical primer pair, the ends of the amplification products will be self-complementary after a few PCR cycles. For the short, target independent, primer dimerization products the formation of intramolecular "panhandle" structures will be favoured, which will protect the 3'-end and prevent further amplification of the primer dimers[9]. The suppression of primer dimers will allow higher multiplexing.

In a related scheme[10], which adapts the PCR suppression concept[11] for multiplex detection, a universal primer target (adaptor) is ligated to the ends of the genomic DNA. The multiplex amplification is achieved by using one primer, common for all multiplex reactions, targeting the adaptor region and one target specific primer for each multiplex component reaction. Two mechanisms are proposed to explain the multiplex efficiency archived with this method[10]. First, the reduction of the number of primers used in the reaction, since the adaptor primer is identical for all reaction, reduces unwanted primer interactions. Secondly, spurious amplification brought about by the adaptor primer alone will produce amplicons with self-complementary ends and hence will form panhandle structures whose further amplification will be suppressed in the same way as proposed for the primer dimers in the HANDS method[9].

Subsequently, the use of universal primers have found many uses in multiplex methods such as multiplex microarray enhanced PCR[12], Templex PCR[13], nested patch PCR[14] but also in ligation based multiplex amplification methods such as multiplex ligation-dependent probe amplification[15] and assays based on sequence tagged molecular inversion probes[16].

Despite the efforts made in the art there is still a need for novel methods that provide homogeneous amplification of all recognized target segments in large sets of genomic sequences.

SUMMARY OF THE INVENTION

The object of the present invention is to provide a novel method that addresses the aforementioned problem of differentiating large sets of genomic sequences by combining several of the themes described above in a new way.

According to the invention differentiation of large sets of genomic sequences is achieved by a semi-nested method comprising pre-amplification and a two-level amplification reaction, which decouples the recognition and detection events.

The invention relates in one aspect to a method for genotyping N loci present in a sample in a target nucleic acid molecule, wherein each locus is located in a genotype marker region of the nucleic acid molecule, and corresponds to two or more genotypes.

In a second aspect, the invention relates to a kit for performing said method for genotyping, comprising primers, and optionally other ingredients of a nucleic acid amplification reaction mixture.

In a third aspect the invention relates to a method for designing and producing selection primers to be used in the method for genotyping or in the kit for performing the genotyping method.

In a fourth aspect the invention relates to a method for producing detection primers to be used in the method for genotyping or in the kit for performing the genotyping method.

In a fifth aspect the invention relates to selection primers adapted for genotyping of loci in a target nucleic acid molecule.

In a sixth aspect the invention relates to a computer program product for designing selection primers.

Further advantages and objects with the present invention will be described in more detail, inter alia with reference to the accompanying drawings.

Definitions

Figure 1:
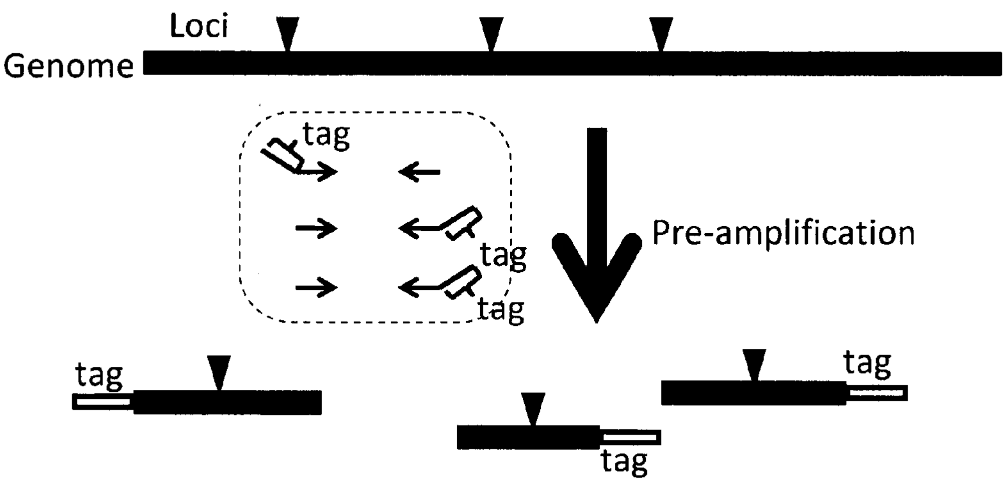
FIG. 1 shows the outline of one embodiment of the pre-amplification step a) of the method for genotyping, wherein some primers are tagged with an artificial sequence.

In the context of the present application and invention, the following definitions apply:

As used herein, the term genotyping refers in a broad sense to the process of determining the particular nucleotide or nucleotides (e.g. sequence variation) either present or absent at a particular polymorphic locus or genomic location. The term genotype refers to the genetic constitution of a cell, an individual or an organism.

By the term locus is meant the specific location of a gene or nucleic acid sequence, such as chromosomal DNA or RNA of any origin, as derived from eukaryots, prokaryots etc. In a bacterial species the locus may be located, besides chromosomal DNA, in mobile elements such as plasmids, transposons, resistance cassettes and virulence genes, and the genotyping will include determination of presence and nature or absence of these elements as well as genotyping of chromosomal loci.

As used herein, the term sample refers to a composition containing a material to be detected or analyzed. Samples include biological samples, which refer to any material obtained from a living source, for example, an animal such as a human or other mammal, a plant, a bacterium, a fungus, a protist or a virus or a processed form, such as amplified or isolated material.

In this context the terms target and bind, and words derived therefrom, are intended to illustrate the event at which, or the site to which, a primer may hybridize under stringent conditions.

By the term genotype marker region is meant a genomic region whose sequence or existence signify a property of the organism such as: genotype, virulence/pathogenicity, presence of mobile element, presence of certain genes, resistance to antibiotics, etc.

As used herein, the term amplifying or amplification refers to means for increasing the amount of a biopolymer, especially nucleic acids. Based on the 5' and 3' primers that are chosen, amplification also serves to restrict and define a target-region or locus of the genome which is subject to analysis. Amplification can be performed by any means known to those skilled in the art, and in particular embodiments include the use of the polymerase chain reaction (PCR).

By the term pre-amplification is meant an amplification system, preferably a PCR system, targeting a DNA genetic material, which may be reversely transcribed RNA, from an organism for which the genotype, e.g. the avian influenza pathotype is to be determined.

By the term primer is meant an oligonucleotide hybridising to a nucleic acid sequence during amplification. The term forward primer is referred to as a primer with the same sequence as the coding strand of a gene or an artificial sequence chimerically joined to the coding strand, and the term reverse primer is referred to as a primer with a sequence complementary to the coding strand of a gene or complementary to an artificial sequence chimerically joined to the complement of the coding strand.

Selection primers are used in a selection amplification system, preferably a PCR system which is to be construed as an amplification system targeting the template provided by the pre-amplification amplification system. Either the reverse or the forward primers target the region, which determines the assayed property, in a multiplexed way by bipartite primers whose 5'-end regions is constituted of artificial sequence elements of different kinds depending on the nature of the genotype signified by the sequence recognizing the 3'-end portion of the bipartite primer. The corresponding reverse/forward primer may or may not be multiplexed.

Detections primers are used in a detection amplification system, preferably a PCR system, which is to be construed as a multiplex amplification system targeting the templates provided by the selection amplification system. Either the reverse or the forward primers may be labelled with labels or chemical moieties for detection.

By the term amplicon is meant a DNA segment formed as the products of natural or artificial amplification events.

The terms nucleic acid and nucleic acid molecule are used interchangeably throughout the disclosure. The terms refer to a deoxyribonucleotide (DNA), ribonucleotide polymer (RNA) and RNA/DNA hybrids in either single- or double-stranded form. The phrase simultaneous amplification refers to the amplification of 2 or more loci or nucleic acid target-regions at the same time. The simultaneous amplification is typically within the same amplification mixture. Although it is contemplated herein that the simultaneous amplifications can occur in separate reaction mixtures, for the methods provided herein the simultaneous amplification reactions typically occur in the same single reaction.

As used herein, the term multiplexing refers to the simultaneous amplification or primer mass extension reaction of more than one oligonucleotide or primer (e.g., in a single reaction container); or the simultaneous analysis of more than one oligonucleotide, for instance in an array reader device; or simultaneous interrogation of the sample by multiple primers.

As used herein, the phrase target nucleic acid refers to one or more nucleic acids, such as genomic DNA, from which one or more regions or loci are to be amplified.

As used herein, the term polymorphism refers to the coexistence of more than one form or allele of a nucleic acid, such as a gene, or portion thereof. For example, a portion or locus of a gene for which there are at least two different alleles, i.e., two different nucleotide sequences, is referred to as a polymorphic loci, site or region of a gene. A polymorphic locus can be a single nucleotide (e.g., SNP) or can be several nucleotides in length (e.g., the avian influenza cleavage site, insertions or deletions). Accordingly, polymorphism includes substitutions, insertions, duplications and deletions of nucleotides. A polymorphism can also refer to a particular nucleotide(s) or nucleotide sequence occurring at a particular polymorphic site.

DETAILED DESCRIPTION OF THE INVENTION

The present invention relates in a first aspect to a method for genotyping N loci present in a sample in a target nucleic acid molecule, wherein N is at least 1 and each locus is located in a genotype marker region of the nucleic acid molecule, and corresponds to two or more genotypes, preferably two genotypes. The method comprises the following steps a) to c).

In step a) a pre-amplification of each genotype marker region is performed utilizing primer-dependent enzymatic reactions. The pre-amplification is performed with a first group of amplification primer pairs consisting of a first set of one or more different forward primers and a first set of one or more different reverse primers, yielding one or more amplicons encompassing the genotype marker region(s). Each amplicon contains a region with at least one nucleotide sequence that can act as a primer binding target distinct from the genotype marker region.

The pre-amplification can be achieved in N separate monoplex reactions or in a single N-plex reaction or anything in between these extremes.

The nucleotide sequence, preferably 10-40 nucleotides long, that can act as a primer binding target belongs to a set of sequences having less than 100 members, preferably less than 20 members and more preferred 1 to 5 members. Said set of sequences may be achieved by the existence of conserved genomic regions on the amplicons, or by using enzymatically connected artificial sequences, for example by ligation or by using bipartite PCR primers containing artificial 5'-end parts, or a combination of these mechanisms. Some embodiments of the pre-amplification step a) is described in FIG. 1.

The sample is a composition containing a material to be genotyped. Samples include biological samples, which refer to any material obtained from a living source, for example, an animal such as a human or other mammal, a plant, a bacterium, a fungus, a protist or a virus or a processed form, such as amplified or isolated material.

The locus or loci of interest may represent specific location(s) of a gene or DNA or RNA sequence determining a specific property, such as the degree of pathogenicity, resistance to antibiotics, etc. The number of loci, N, to be genotyped is preferably between 1 and 10 000, more preferred 1 to 100, most preferred 1.

The magnitude of the pre-amplification may be sufficient for direct detection by means such as gel electrophoresis or real-time PCR but may also be lower than typically required for direct detection.

In step b) a two-level nucleic acid amplification reaction utilizing primer-dependent enzymatic reactions is performed on the amplicon(s) from step a), step b) comprising the following two steps b1) and b2).

The first level, step b1) is a nucleic acid amplification utilizing a second group of primer pairs binding to each amplicon produced in step a). Said group of primer pairs consists of a second set of one or more different forward primers and a second set of one or more different reverse primers, wherein each sequence variant of each locus is targeted by at least one primer from said second sets of primers, said at least one primer forming a set of selection primers. In contrast to conventional primer design, a region with large variation should be selected for the selection primer binding target, where differences between genotypes appear clearly. The selection primers are bipartite having at the 3'-end a locus recognition sequence part that binds to either of said N loci at the genotype marker region and at the 5'-end an artificial one-piece tagging sequence part that is genotype specific or an artificial two-piece tagging sequence part, wherein one piece is genotype specific and the other one is non-genotype specific. Each selection primer that binds to the target locus of the genotype marker region forms a primer pair together with another primer belonging to said second sets of primers but targeting said nucleotide sequence that can act as a primer binding target of step a). It is preferred that each selection primer is present in a concentration of less than 100 nM, preferably of 10-0.01 nM, and most preferred approximately 0.1 nM, and the other primer of said primer pair is present in a concentration of at least 100 times, preferably between 100 and 100 000 times that of said selection primer. This step b1) yields amplicons each containing a respective one of said N loci.

The binding, or targeting, of a bipartite selection primer to either of said N loci should occur by hybridization of said primer to the genotype marker region containing the locus, under stringent conditions. The number of mismatches between the genotype marker region and the selection primer should be less than 5, preferably less than 4, more preferred no more than 1, and most preferred 0.

The low concentration of selection primers allow very high multiplexing (at least 10-1000). A high number of different selection primers may be used simultaneously in the method, such as 10 000 primers, more preferred 1000 to 100 primers. Due to the very robust character of the method for genotyping the total number of different selection primers that may be used for the simultaneous amplification may easily be increased if required, e.g. as a consequence of mutations leading to not previously known sequences demanding new primers for detection.

The selection primers may also be degenerate allowing for detection of very similar sequences within the same genotype by means of variants of the same primer. The concept of degenerate primers is well known in the art. In nucleic acid sequences of degenerate oligonucleotides (primers) R is either A or G, Y is C or T, M is A or C, K is G or T, W is A or T, S is C or G, B is C, G or T, D is A, G or T, H is A, C or T, V is A, C or G, and N is A, C, G or T.

The concentration of said other primer is at least 100 times that of said selection primer and may be in the range of 100 to 0.01 μM, preferably 10-0.01 μM, and most preferred approximately 0.3 μM.

The second level, step b2) is a nucleic acid amplification utilizing a third group of primer pairs binding to each amplicon produced in step b1). This group of primer pairs, present in a concentration of at least 100 times, preferably between 100 and 100 000 times that of said selection primers in step b1), consists of a third set of one or more different forward primers and a third set of one or more different reverse primers. Each tagging sequence part of each selection primer is targeted by at least one primer from said third sets of primers, wherein said at least one primer forms a set of detection primers, and wherein each detection primer that binds to the tagging sequence part forms a primer pair together with another primer belonging to said third sets of primers but targeting said nucleotide sequence that can act as a primer binding target of step a). The detection primers preferably have:

i) a genotype-specific sequence corresponding to the artificial one-piece tagging sequence part of the selection primers, wherein each detection primer is labelled with a genotype-specific detectable label; or ii) a non-genotype specific sequence which is common to all detection primers and corresponds to the non-specific sequence of the artificial two-piece tagging sequence part of the selection primers, wherein each detection primer is optionally labelled at the 5'-end with a detectable label or a chemical moiety.

Step b2) results in detectable amplicons each containing a respective one of said N loci labelled with genotype specific tagging sequences and, optionally, genotype specific labels.

Said detection primers may be labelled with a label selected from the group consisting of fluorophores, luminescent labels, radiolabels, enzymatic labels, chromophores, such as Biosearch Blue™, Acridine, Coumarine, FAM, Rhodamine Green, TET Cal Fluor® Gold 540, JOE, VIC, HEX, CAL Fluor Orange 560, Quasar® 570, TAMRA, Rhodamine Red, CAL Fluor 590, Cy3.5, ROX, CAL Fluor Red 610, CAL Fluor REd 635, Pulsar(R) 650, Quasar 670, and Quasar 705, and one member of a binding pair, such as biotin and streptavidin.

The concentration of the primers belonging to said third group of primer pairs may be in the range of 100-0.01 μM, preferably of 10-0.01 μM, and most preferred approximately 0.3 μM.

In step c) the genotyping of said N loci of the target nucleic acid molecule is performed by:

c1) during, or optionally after, the amplification thereof detecting each label comprised in each amplicon produced in step b2i), and relating the predominant amount of detected label to a specific genotype for each locus; or c2) after amplification contacting each amplicon produced in step b2ii) with a detection array of genotype specific sequences, detecting the hybridization of each amplicon to the array, and relating the detected hybridization to a specific genotype for each locus.

The genotyping of step c1) may advantageously be performed by means of real-time PCR, but other amplification techniques obvious to the skilled person may also be conceivable. The genotyping of step c2) may advantageously be performed by means of a detection array such as a microarray assay, but other techniques known to the skilled may also be used.

One way of performing the genotyping of step c1) is by using detections primers which adjacent to a label in the 5'-end have an iso-dC nucleotide. The amplification is performed in the presence of dabcyl-iso-dGTP, and the detection in step c1) occurs when the dabcyl-iso-dGTP quenches label signals when incorporated opposite to iso-dC. In case the locus or loci to be genotyped correspond to two genotypes the difference between label signals may be calculated, in order to achieve a more robust assay. By monitoring the difference signal or the signal ratio from labelled primers, a straightforward positive-or-negative detection scheme allows swift and simple typing.

The proper conditions for amplification are well known in the art, and depend e.g on annealing temperature and time, type of buffer, additives, primer concentrations, number of cycles etc. and are well known to a person skilled in the art. The amplifications according to the method for genotyping is preferably stringent conditions.

The selection primers and detection primers may have sequences selected to minimize primer-primer interaction. This can be achieved e.g. by partially self complementary primers. Advantageously the artificial tagging sequence part of said selection primers has self complementary ends to form less than 10 base pairs, preferably of 3-7 base pairs, and most preferred 5 base pairs. One way of minimizing primer-primer interaction is by forming panhandle structure, see FIG. 4.

It is preferred that all primers used in the above method are constructed to have melting temperatures within a range of about 10° C., preferably 5° C., and more preferred 1° C. from each other.

In one embodiment of the method for genotyping said at least one sequence that can act as a primer binding target of step a) corresponds to an artificial sequence tagging part introduced in the amplicons formed in step a) by means of said first set of primers, wherein said primers are bipartite and comprise an artificial 5'-tagging sequence, and a 3'-region binding to the target nucleic acid molecule. In another embodiment said at least one sequence that can act as a primer binding target of step a) corresponds to genomic regions.

In one preferred embodiment said third set of primers used in step b2) binding to the at least one sequence that can act as a primer binding target of step a) is the same as said second set of primers used in step b1) binding to the at least one sequence that can act as a primer binding target of step a). In another preferred embodiment said second set of primers used in step b1) binding to the at least one sequence that can act as a primer binding target of step a) is the same as either first set of primers used in step a).

The selection primers and the detection primers may belong to said sets of forward primers or to said sets of reverse primers.

Each locus of said N loci corresponds to two or more genotypes, preferably two genotypes. These two genotypes may indicate high pathogenicity and low pathogenicity, respectively, of a microorganism whose genome contains said locus. The two genotypes may also correspond to the presence or absence of a locus, indicating e.g. antimicrobial resistance and non-resistance, respectively of microorganisms. The presence or absence of a locus could e.g. indicate resistance to antibiotics. The microorganism may be a virus, such as an influenza virus, a bacteria. etc.

Step a), b1) and b2) may be carried out in the same reaction tube, may be carried out in separate reaction tubes or with any of the steps a), b1) and b2) carried out in a separate reaction tube but the other two steps in the same reaction tube. When carrying out two steps in the same reaction tube, a multicompartment tube may be used, such as the one described in WO2006066245(A2).

Figure 2:
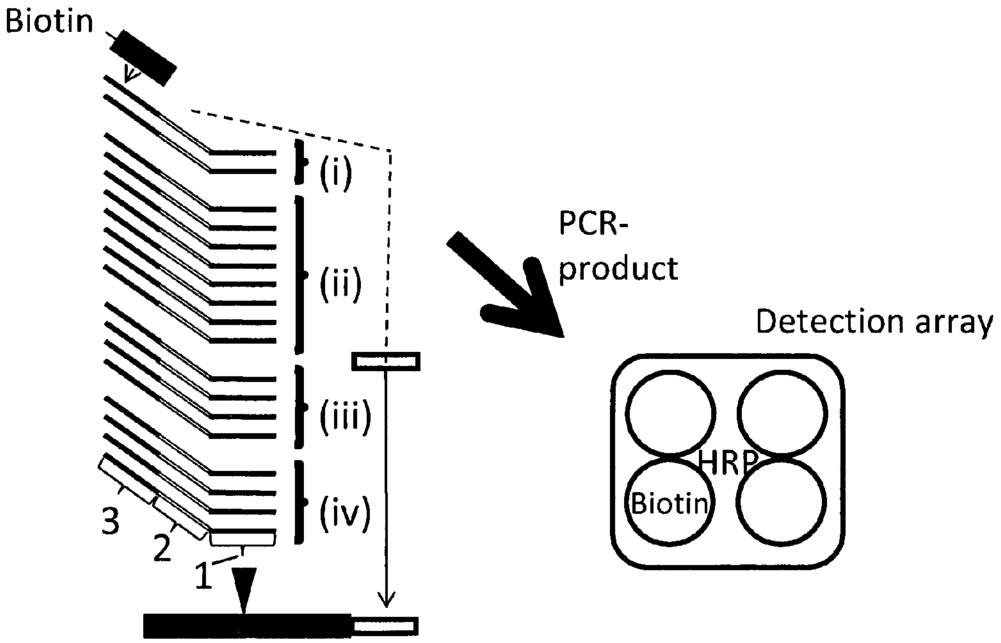
FIG. 2 shows the outline of one embodiment of step b) of the method for genotyping, in which one locus is to be genotyped corresponding to four genotypes. The selection primers (forward primers) are bipartite with a locus recognition sequence part (1), and an artificial two-piece tagging sequence part in which one piece is genotype specific sequence (2) composed of structure free DNA word for array hybridization and the other piece is a non-genotype specific sequence (3) common to all bipartite selection primers. The detection primer (forward primer) is common to all genotypes and corresponds to the non-genotype specific sequence of the selection primers. The reverse primer is the same for both selection and detection. The DNA word (barcode sequence) corresponds to a sequence on a readout array. Normally the array carry the same sequences as the DNA word to avoid direct binding of the bipartite primers and binding will require a round of PCR amplification to create the complement of the DNA word.
Figure 3:
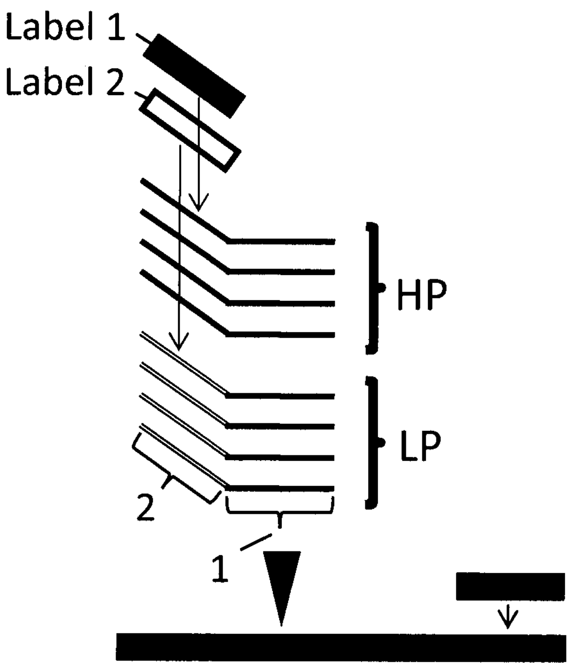
FIG. 3 shows the outline of one embodiment of step b) of the method for genotyping, in which one locus is to be genotyped corresponding to two genotypes of influenza virus (HP=high pathogenicity, LP=low pathogenicity). The selection primers (forward primers) are bipartite with a locus recognition part (1) and an artificial one-piece genotype-specific tagging sequence part (2). Two detection primers (forward primers) are used, and labelled with label 1 and label 2, respectively, corresponding to the respective genotype. The reverse primer is the same for both selection and detection.

FIGS. 2 and 3 show embodiments of step b), wherein bipartite selection primers having an artificial two-piece tagging sequence are exemplified in FIG. 2 and bipartite selection primers having an artificial one-piece tagging sequence are exemplified in FIG. 3.

In one embodiment of the method for genotyping one specific locus, a cleavage site in an avian influenza virus, is genotyped. Said cleavage site will upon cleaving confer high pathogenicity and low pathogenicity, respectively, to the virus. Hence the high and low pathogenicity corresponds to two genotypes. A primer pair is used in step a) which consists of primers comprising the nucleic acid sequences of SEQ ID NOs: 59 and 58, or of primers comprising the nucleic acid sequences of SEQ ID NOs: 57 and 56. The selection primers of step b1) are chosen from oligonucleotides comprising the sequences of SEQ ID NOs: 1 to 55, whereas the detection primers comprise the sequences of SEQ ID NO:s 60 and 61. In a preferred embodiment thereof said detection primers have an iso-dC nucleotide adjacent to the label in the 5' end, and the amplification of step b2) is performed in the presence of dabcyl-iso-dGTP, wherein the dabcyl-iso-dGTP quenches label signals when incorporated opposite to iso-dC.

Considering the serious epidemiological threat posed by highly pathogenic influenza viruses worldwide, the method of the invention is exemplified by an avian influenza pathotyping assay, where the sample is interrogated for almost 400 different cleavage sites in two large sets of genomic sequences. However the method should also be useful in all areas of genomic research where similar problems occur.

An avian influenza pathotyping assay for all avian influenza viruses isolated to date in the Eastern hemisphere has been constructed. The method relies on a semi-nested PCR construct that, in the case of the AIV pathotyping assay, allows almost a 400-plex interrogation of the sample, which covers all relevant sequence variants that, according to our knowledge, have occurred in the Eastern hemisphere to date. The high level of multiplexing is only effective during the recognition event and is reduced to a two-color real-time PCR detection by the use of universal fluorogenic panhandle primers. It is shown that the method provides a fast and simple alternative to DNA sequencing, which can be implemented for large sample screening or on portable PCR machines for field diagnostics.

Occurrence of cleavage sites characteristic for high- or low-pathogenic viruses is indicated by a positive or negative fluorescence ratio signal, respectively. It is shown that the assay concept is extensible, versatile, robust and highly efficient. Proteolytic posttranslational cleavage is a common requirement for virus activation and frequently coupled to pathogenicity. Thus, the assay technique should find broad application in basic viral research as well and diagnostic applications and in general typing applications in all fields of genomics. Avian influenza virus pathotyping amounts to the problem of discriminating all RNA sequences leading to the amino acid motif: R/K-X-R/K-R from all other possible nucleotide sequences. This is a formidable probing problem considering that more than 18,000 nucleic acid sequences can result in this series of amino acids. For this reason, AIV pathotyping is typically done by DNA sequencing rather than probe based assays[7]. From all geographic locations, excluding the Americas, in early 2009 isolates of the H5 and H7 subtypes had been discovered with about 240 unique cleavage site sequences as evidenced by their presence in the NCBI databank[21]. However, this number steadily increases due to the immunological pressure from the broad spectrum of host species that may harbor influenza viruses, leading to alterations in the surface exposed glycoproteins, notably the haemagglutinin protein, which determines pathogenicity.

To solve this problem we exploited a novel strategy for highly multiplexed DNA sequence interrogation of a sample by separation of the recognition and detection events in a two-level PCR system construct. By lowering the concentration of the sequence recognizing primers (the selection primers) thousand times, we were able to design a 380-plex primer mixture for recognition of the whole set of existing cleavage sites (the oversampling is due to the use of degenerate primers producing some sequence not so far discovered in nature). The lowering of the concentration of the selection primers is made possible by pre-amplifying the target and effectively reverse the recognition event. The detection is linked to the pathogenicity of the cleavage site via two Plexor® primers[17] with different fluorescent labels and sequence, which target the artificial 5"-regions of the two sets of bipartite selection primers that in turn targets low- and high-pathogenic cleavage sites. By using a duplex real-time PCR format, the pathotyping reaction can be carried out in a single tube and we allow the two sets of cleavage site recognizing primers (the selection primers) to compete for binding to the target (i.e., the cleavage site). In this way, we avoid requiring absolute specificity of the assay, it is sufficient that a cleavage site of a sample under investigation is more similar to one or the other of the two sets of selection primers to deduce the pathogenicity. We find it convenient to monitor the ratio signal obtained from the two detection primers to determine the preferential amplification of one of the sets of selection primers over the other. Furthermore, by giving the detection primers self-complementary ends (panhandle primers) spurious priming and non-specific signals were greatly suppressed. The mechanism here is different from previous investigators' use of the panhandle concept, who either used chimerical primers with universal 5'-end region to suppress primer dimers[9] or universal ligated adaptor sequences to suppress spurious priming on the target[10]. In the present case, the primers themselves form panhandles. The strong intra- and inter-molecular base pairings that will be formed by the panhandle primers protect the 3∝-end and compete out alternative pairing schemes that could provide a substrate for the DNA polymerase. In addition, we speculate that the panhandle shaped 5'-end of the bipartite selection primers could work as a charge load that repel other primers leading to decreased interactions between primers. Attempts to construct the detection primers from structure free DNA word sets[22], were unsuccessful since these primers seemed to easier initiate priming within the selection primer set (data not shown). It is interesting to note that one of the first studies utilizing universal primer tags in multiplex PCR also used a universal primer that could form a hairpin structure with five GC-base pairs[23].

The present strategy provides a remarkably effective and robust assay for avian influenza virus pathotyping. All isolates carrying cleavage site sequences that had been accounted for in the selection primer sets were correctly pathotyped. Only when either the pre-amplification failed or when novel cleavage sites were encountered, did the assay fail. The assay is very flexible since new selection primers easily can be added when viruses with novel cleavage sites emerge and any pre-amplification primers can be used as long as they encompass the cleavage site. It must be emphasized that the pathotyping assay is not a detection assay requiring thorough optimization for appropriate sensitivity. This makes the assay very robust and insensitive to the exact PCR temperature profile used and the purity and concentration of the primers. These requirements are instead shifted to the pre-amplification system. Although the selection primers are about twice as long as normal primers and a set of 55 degenerate selection primers were used in the present study, the additional cost for the pathotyping assay is negligible. This is due to the dilution by a factor of thousand compared to a typical primer concentration which reduces the cost per reaction for the whole set of 55 primers to only ten percent of the cost of a single conventional primer. Since the assay relies on a semi-nested format, carry-over contaminations could be an issue. However, the inherent insensitivity of the pathotyping assay with a three orders of magnitude lower concentration of the sequence recognizing primers makes the assay much less prone to this problem than conventional nested PCR approaches.

This pathotyping assay provides new opportunities for avian influenza surveillance and diagnostics, since it has the capacity to substitute the currently used expensive, cumbersome and time-consuming sequencing procedures and to enable faster diagnostics with the advantage of simplified sample transportation to field laboratories in the vicinity of the outbreaks. The method should also be ideal for implementation on portable PCR machines even without real-time reading due to the simple positive/negative signal readout that can be used to differentiate the pathotypes. Another application is the high throughput screening by multiplex interrogation for sequences of interest. Although we in the present study have exemplified the assay strategy with avian influenza virus pathotyping, proteolytic posttranslational cleavage is a common requirement for virus activation and, for example, for the Newcastle virus and the Sendai virus cleavage has been connected to pathogenicity[1,2]. Considering the illustrated strengths, it is supposed that this technique will find a broad applicability in basic and in applied virology, in central diagnostic institutes as well as simply equipped field laboratories.

Furthermore, the method provides novel means for a wide range of general typing applications in all fields of genomic biotechnology.

Any other use of the inventive method for typing of large sets of genomic sequences is also conceivable, such as for differentiation between bacteria showing antibiotic resistance and non-resistance, respectively.

In a second aspect the invention relates to a kit for performing the above method for genotyping, comprising a first group of primer pairs consisting of a first set of one or more different forward primers and a first set of one or more different reverse primers for performance of the pre-amplification step a) of the method, a second group of primer pairs consisting of a second set of one or more different forward primers and a second set of one or more different reverse primers, one second set of which forms a set of selection primers, wherein the selection primers are bipartite and have at the 3'-end a locus recognition sequence part and at the 5'-end an artificial one-piece tagging sequence part being genotype specific or an artificial two-piece tagging sequence part, one piece thereof being genotype specific and the other one being non-genotype specific, for performance of the first level amplification of step b1) of the method; a third group of primer pairs consisting of a third set of one or more different forward primers and a third set of one or more different reverse primers, one third set of which forms a set of detection primers, wherein the detection primers either have a genotype-specific sequence corresponding to the artificial one-piece tagging sequence part of the selection primers or a non-genotype specific sequence common to each detection primer and corresponding to the non-specific sequence of the artificial two-piece tagging sequence part of the selection primers, for performance of the second level amplification of step b2) of the method, wherein the detection primers are optionally labelled at the 5' end with a label or a chemical moiety, and optionally other ingredients of a nucleic acid amplification reaction mixture.

It is advantageous for said selection primers or detection primers to have sequences selected to minimize primer-primer interaction. This may be achieved by providing primers with self complementary ends that form less than 10, more preferably 3-7 and most preferred 5 base pairs. The self complementary ends may form panhandles, as described earlier.

The detection primers are preferably labelled with a label or chemical moiety selected from the group consisting of fluorophores, luminescent labels, enzymatic labels, radio labels, chromophores and one member of a binding pair, such as biotin or streptavidin. Examples include Biosearch Blue™, Acridine, Coumarine, FAM, Rhodamine Green, TET Cal Fluor® Gold 540, JOE, VIC, HEX, CAL Fluor Orange 560, Quasar® 570, TAMRA, Rhodamine Red, CAL Fluor 590, Cy3.5, ROX, CAL Fluor Red 610, CAL Fluor REd 635, Pulsar(R) 650, Quasar 670, and Quasar 705.

In one embodiment said third set of forward primers is the same as said second set of forward primers, or said third set of reverse primers is the same as said second set of reverse primers. In another embodiment said second set of forward primers is the same as said first set of forward primers, or said second set of reverse primers is the same as said first set of reverse primers.

In one preferred embodiment for performing genotyping of avian influenza virus, the kit comprises the first sets of primers comprising the sequences of SEQ ID NOs: 59 and 58, or the sequences of SEQ ID NOs: 57 and 56, selection primers chosen from oligonucleotides comprising the sequences of SEQ ID NOs: 1 to 55, and detection primers chosen from oligonucleotides comprising the sequences of SEQ ID NO:s 60 and 61.

The kit may include detection primers comprising an iso-dC nucleotide adjacent to the label in the 5' end, and the nucleic acid amplification reaction mixture then comprises dabcyl-iso-dGTP.

In a third aspect the invention relates to a method for designing and producing selection primers to be used in the method for genotyping or in the kit for performing the genotyping method. The method comprises the following steps a) to g). Steps a) to e) is preferably performed by means of one or several computer programs.

In step a) a large number of nucleic acid molecule sequences of interest are aligned, which comprise at least one locus. In step b) the the aligned nucleic acid molecules sequences are merged by means of a computer program with profile alignment function. The aligned nucleic acid molecules sequences are in step c) trimmed to oligonucleotides having between 20 and 50 nucleotides, preferably between 30 and 40 nucleotides, more preferred 35 oligonucleotides, covering said locus, and in step d) the length of said oligonucleotides of step c), is adjusted to achieve similar melting temperatures for all of said oligonucleotides. The melting temperatures of said oligonucleotides are preferably within an interval of about 10° C., preferably within 5° C., more preferred within 1° C. Step e) refers to the grouping of said oligonucleotides into degenerate primers, and step f) refers to the synthesizing of said degenerate primers while adding to the 5' end of the primers an artificial one-piece tagging sequence part that is genotype-specific or an artificial two-piece tagging sequence part, wherein one piece thereof is genotype specific and the other one is non-genotype specific. Finally, in step g) selection primer product of step f) is recovered.

The artificial tagging sequence part of the selections primers may have a sequence selected to minimize primer-primer interaction, e.g. by being self complementary to form less than 10, more preferably 3-7 and most preferred 5 base pairs.

The nucleic acid molecule sequences of step a) preferably originate from a microorganism, such as a virus, bacteria, etc. The nucleic acid molecule sequences of step a) may e.g. originate from influenza virus and the target nucleic acid sequence of interest may e.g. be the haemagglutinin precursor protein cleavage site. This cleavage site correponds to two genotypes representing high pathogenicity and low pathogenicity according to criteria known in the art. The pathogenicity is conferred to the virus upon cleavage of said cleavage site.

The nucleic acid molecule sequences of step a) originating from a bacterial species may, besides chromosomal DNA, include mobile elements such as plasmids, transposons, resistance cassettes and virulence genes, and the genotyping will include determination of existence and nature or non-existence of these elements as well as genotyping of chromosomal loci.

In a fourth aspect the invention relates to a method for producing detection primers to be used in the method for genotyping or in the kit for performing the genotyping method. This method comprises the steps of synthesizing nucleic acids molecules having sequences which correspond to the genotype specific artificial one-piece tagging sequence part of the selection primers, or correspond to the non-genotype specific sequence common to each detection primer and corresponding to the non-specific sequence of the artificial two-piece tagging sequence part of the selection primers. The detection primers are optionally labelled at the 5' end with a label or a chemical moiety selected from the group consisting of fluorophores, luminescent labels, enzymatic labels, chromophores, radio labels and one member of a binding pair, such as biotin or streptavidin. Examples include Biosearch Blue™, Acridine, Coumarine, FAM, Rhodamine Green, TET Cal Fluor® Gold 540, JOE, VIC, HEX, CAL Fluor Orange 560, Quasar® 570, TAMRA, Rhodamine Red, CAL Fluor 590, Cy3.5, ROX, CAL Fluor Red 610, CAL Fluor REd 635, Pulsar(R) 650, Quasar 670, and Quasar 705.

In a fifth aspect the invention relates to selection primers adapted for genotyping of loci in a target nucleic acid molecule, wherein each locus is located in a respective genotype marker region of the nucleic acid molecule, and corresponds to two or more genotypes. The selection primers comprise at the 3'-end a locus recognition sequence part and at the 5'-end an artificial one-piece genotype specific tagging sequence part or an artificial two-piece tagging sequence part, in which one piece is genotype specific and the other one is non-genotype specific.

In one embodiment the part of the selection primers that will cover a locus of interest has a length of 15 to 50 nucleotides, preferably 15 to 30 nucleotides, and more preferred 23 nucleotides. Selection primers are preferred that yield an average melting temperature of approximately 60° C. In another embodiment the selection primers comprise the sequences of SEQ ID NOs: 1 to 55.

In a sixth aspect the invention relates to a computer program product for designing selection primers. The computer program product comprises computer readable instructions that are directly downloadable into the internal memory of a computer. These readable instructions are adapted to induce the computer to design the selection primers according to the invention.

The following examples are intended to illustrate, but not to limit, the invention in any manner, shape, or form, either explicitly or implicitly.

EXAMPLE 1

Viral RNA extraction. Viral RNA was extracted from all isolates except the EU AI PCR Proficiency Panel 2008, using the MagAttract Virus Mini M48 Kit (Qiagen, Hilden, Germany) in the Magnatrix 8000+ extraction robot (NorDiag AB, Hägersten, Sweden) according to the manufacturer's protocol. A sample volume of 100 µl of each virus isolate was used and eluted in 70 µl RNase-free water containing 0.04% sodium azide and used immediately or otherwise stored at −70° C. until use. The EU AI PCR Proficiency Panel 2008 was extracted by using the QIAamp Viral RNA Mini Kit (Qiagen, Hilden, Germany) according to the manufacturer's instructions. Samples from the Freidrich-Löffler-Institute (FLI) and the Epizone AI RNA Panel 2009 were obtained as extracted RNA.

Reverse transcription and pre-amplification. Reverse transcription of the extracted RNA and DNA pre-amplification of all H5 and H7 samples utilized the H5-kha-1/H5-kha-3 and GK7.3/GK7.4, primers, respectively, as recommended by the EU reference laboratories[7]. Both PCR systems were performed in 25 µl reaction volumes using the OneStep RT-PCR kit (Qiagen, Hilden, Germany) with primers at 1 µM concentrations and adding 2.5 µl of the extracted viral RNA in each reaction. The cycling conditions for the H5-kha-1/H5-kha-3 PCR system were: 30 min reverse transcription at 50° C.; 15 min enzyme activation/deactivation at 96° C.; 40 cycles of: 96° C. for 10 sec, 58° C. for 30 sec, 68° C. for 30 sec; and a final extension step at 68° C. for 7 min. The cycling conditions for GK7.3/GK7.4 were: 30 min reverse transcription at 50° C.; 15 min enzyme activation/deactivation at 95° C.; 35 cycles of: 94° C. for 30 sec, 52° C. for 30 sec, 72° C. for 45 sec; and a final extension step at 72° C. for 4 min and 15 sec. All amplifications were verified by agarose gel electrophoresis using pre-cast E-gel 2% with ethidium bromide (Invitrogen, Carlsbad, Calif.) and visualized under UV-light. The expected amplicons sizes were 300-320 and 200-220 for H5 and H7 amplifications, respectively. A subset of samples were reverse transcribed and pre-amplified with a One-Step reactions utilizing universal primers designed to amplify all AIV subtypes as previously described[20], with the exception that the 5'-end overhang sequences of the reverse primers used for the purpose of sequencing in the original study were removed.

Primer design. All H5 and H7 haemagglutinin gene sequences derived from isolates outside of the Americas and available at the NCBI influenza virus resources[21] were collected in February 2009 amounting to 2305 sequences. The sequences were divided in four sets: H5N1; all other H5; H7N1+H7N3+H7N7; all other H7, which were separately aligned with Muscle 3.6[24] using default setting. Due to the large number of H5N 1 sequences, these sequences were divided in two sets that were aligned separately to reduce memory requirements. These two aligned sets were then merged with the profile alignment function of Muscle[24]. The alignments were trimmed to 35-mers ending four bases downstream of the glycine codon of the cleavage site (R↓G) of HAO and redundant sequences were removed using Jalview 2.4[25]. On the basis of these sequences primers were designed. The primers were manually adjusted to have a melting temperature close to 60° C., as calculated by the method by Rychlik et al.[26], by removing 3'- and 5'-end bases from the 35-mers as required while attempting to make the primers cover at least some of the nucleotides of the R↓G codons. This goal was in most cases achieved. After these adjustments occurrence of redundancy were removed again and, finally, 235 sequences remained. To reduce synthesis requirements, the sequences were manually grouped into degenerate primers. The degeneracy was limited to 32 and no adjustments of concentrations were done for the degenerate primers. After introduction of degeneracy, the total number sequences increased to 382 resulting from 55 primers (SEQ ID NOs 1-55). Primers targeting cleavage sites of the high-(32 primers) and low-(23 primers) pathogenic genotype carried a CGGGAACTATCACCAAACAACACCCCG and a CGGGACAACAAACCACTATCAACCCCG 5'-overhang, respectively. The four terminal GC-basepairs at each end of these overhangs are identical in the two sequences and are self-complementary while the remaining internal portion differs by one being the reverse sequence of the other. This group of 55 bipartite, partly degenerate, primers constitute the selection primer set, which interrogate the sample for 382 distinct cleavage site sequences. The Plexor® primers[17] for detection of high- and low pathogenic cleavage sites, have the same sequence as the overhang part of the corresponding bipartite selection primers but are labeled at the 5'-end with FAM and CAL Orange-560, respectively. The reverse primers used in the two-level pathotyping assay are common for both levels and identical to the reverse primers of the pre-amplification systems used. However, although the pre-amplification systems are separate for H5 (H5-kha-1/H5-kha-3) and H7 (GK7.3/GK7.4) the reverse primers are co-added in the pathotyping assay into a single reaction mixture.

Real-time PCR experiments. All selection primer concentrations were 0.3 nM and detection and reverse primer concentrations were 0.3 µM. Selection primers were obtained desalted and dissolved in water at 100 µM from Sigma-Aldrich and were used without further purification. Plexor® primers were obtained from Biosearch Technologies (Novato, Calif.) and the Plexor® qPCR System reagents from Promega (Madison, Wis.). All real-time PCR experiments were carried out on RotorGene 3000 instruments (Corbett Research, Sydney, Australia). The default FAM and JOE channels were used to excite and acquire the signal from the FAM and CAL Orange-560 labelled primers, respectively. Using the RotorGene 3000 standard software analysis tools the raw JOE channel signals were normalized against the raw FAM channel signals and a baseline correction were made. The amplification was achieved by 30 cycles of: 10 sec at 95° C, 15 sec at 50° C. and 20 sec at 72° C., following an initial hold time of 3 min at 95° C.

DNA sequencing. PCR-products from the pre-amplification were treated with Exonuclease/Shrimp Alkaline Phosphatase (ExoSAP-IT) (USB Corporation, Staufen, Germany) at 37° C. for 15 min to degrade remaining primers and nucleotides and before use in cycle sequencing with the Big Dye Terminator v3.1 cycle sequencing kit (Applied Biosystems, Foster City, Calif.). Reaction volumes were 5 μl with 7.5 pmol of each primers H5-kha-1/H5-kha-3 and GK7.3/GK7.4 for H5 and H7 subtype samples, respectively. The cycling conditions were: 25 cycles of 96° C. for 15 sec, 50° C. for 10 sec and 60° C. for 2 min. The products were purified by using Montage SEQ96 Sequencing Reaction Cleanup Kit (Millipore Corporation, Billerica, Mass.) and subsequently analyzed on an ABI Prism 3130x1 capillary sequencer (Applied Biosystems, Foster City, Calif.). Sequence data were analyzed and edited with the DNAstar software package (DNASTAR, Madison, Wis.)

Results

Figure 4:
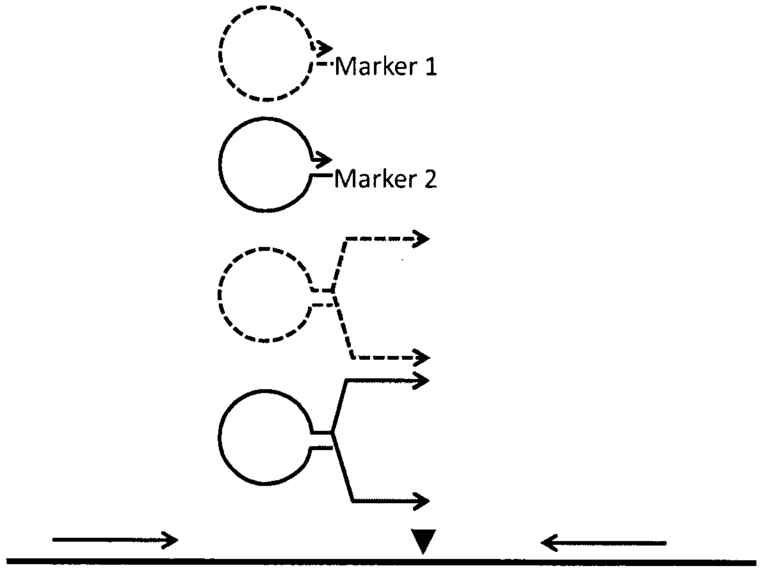
FIG. 4 shows the outline of the scheme for one embodiment of the method for genotyping. Here the method is a semi-nested pre-amplification and two-level real-time PCR method used for avian influenza virus (AIV) pathotyping. A triangle marks the cleavage site, i.e. the locus to be genotyped. Black arrows denote the pre-amplification primers. Bipartite selection primer sets for recognition of cleavage sites characteristic for high- and low-pathogenic viruses are depicted as panhandle shapes connected to a rectangular region that symbolizes the sets of target recognizing sequences. The detection primers are shown as panhandle shapes labelled with a label. Solid and dashed lines signify whether the primers recognize/detect cleavage sites typical for high- or low-pathogenic viruses, respectively. The self-complementary panhandle shapes serves the purpose to minimize primer-primer interactions.

With the goal to achieve highly multiplexed interrogation of a sample for detection of distinct sequences that fall into two categories, a three-level semi-nested PCR assay construct was devised (FIG. 4). The assay exhibits four salient features. First, a larger genomic region encompassing the region under investigation is pre-amplified by PCR. Consequently, the assay requires that known conserved primer regions exist on either site of the sequence segment under investigation. For the subsequent actual pathotyping PCR assay, the vast increase of the amount of template by PCR, allows the primer concentration to be lowered, which will permit a high degree of multiplexing since interactions between primers will be suppressed. In fact, under the assay conditions, the template concentration may be higher than that of the target recognizing primers and there is a reverse recognition event. In contrast to most PCR assays, the target recognizing primers directly bind to the region of interest by design, i.e., to the cleavage site, and "probe" the nature of the binding region. However, the low concentration of the target recognizing primers prohibits detection of the amplification product of these primers directly. For his reason these primers are bipartite with a 5'-region which is independent of the target but of two different kinds depending of the nature of the sequence recognizing part of the primers (in our case high- or low-pathogenic cleavage sites). Corresponding to each of the two artificial sequence portions of the target recognizing bipartite primers, i.e., sharing the same sequence, is an additional primer that in contrast to the bipartite primers are at high concentration and also carries a fluorescent label. Thus, the second outstanding feature of the assay is a two-level PCR system with bipartite sequence recognition primers, which upon recognition of the target DNA will be extended and form the target for the second set of target independent artificial primers at high concentration. We denote the former selection primers since the target will select which set of primers are extended, and the latter detection primers. Note that all three PCR systems, the pre-amplification system and the two-level pathotyping system, utilize the same reverse primer and that in total, together with the pre-amplification PCR, there is a three-level PCR system. To reduce self-interactions and spurious priming the detection primers and thus the 5'-regions of the selection primers were given a "panhandle" structure. The extensive secondary structures formed within the primers constitute the third novel feature of the assay and is in stark contrast to conventional primer design since both intramolecular and intermolecular structures can be formed. However, all these structures serve the purpose of protecting the 3'-end and to, in the case of the selection primers, constitute a "charge load" that will repel other primers and minimize primer self-interactions. Finally, the fourth characteristic property of the assay concerns the means of detecting and analyzing the amplification product. The detection principle relies on preferential amplification of one of the sets of PCR products stemming from the selection primers over the other. This is assessed by labeling the two detection primers with a distinct fluorophor (FAM and CAL orange-560 in the pathotyping assay) and measure the the difference or the ratio of the signals in real-time. Since the assay contains no probes, the Plexor® fluorogenic primer technology was used for detection[17]. In contrast to most real-time PCR technologies, the fluorescence decreases upon extension of the primers in the Plexor® technology[17]. In the AIV pathotyping assay the signal from the detection primer for low pathogenicity is divided by the signal from the detection primer for high pathogenicity. Consequently, a sample containing an avian influenza virus exhibiting high pathogenicity will yield a positive signal while low pathogenic viruses will yield negative signals.

Figure 9:
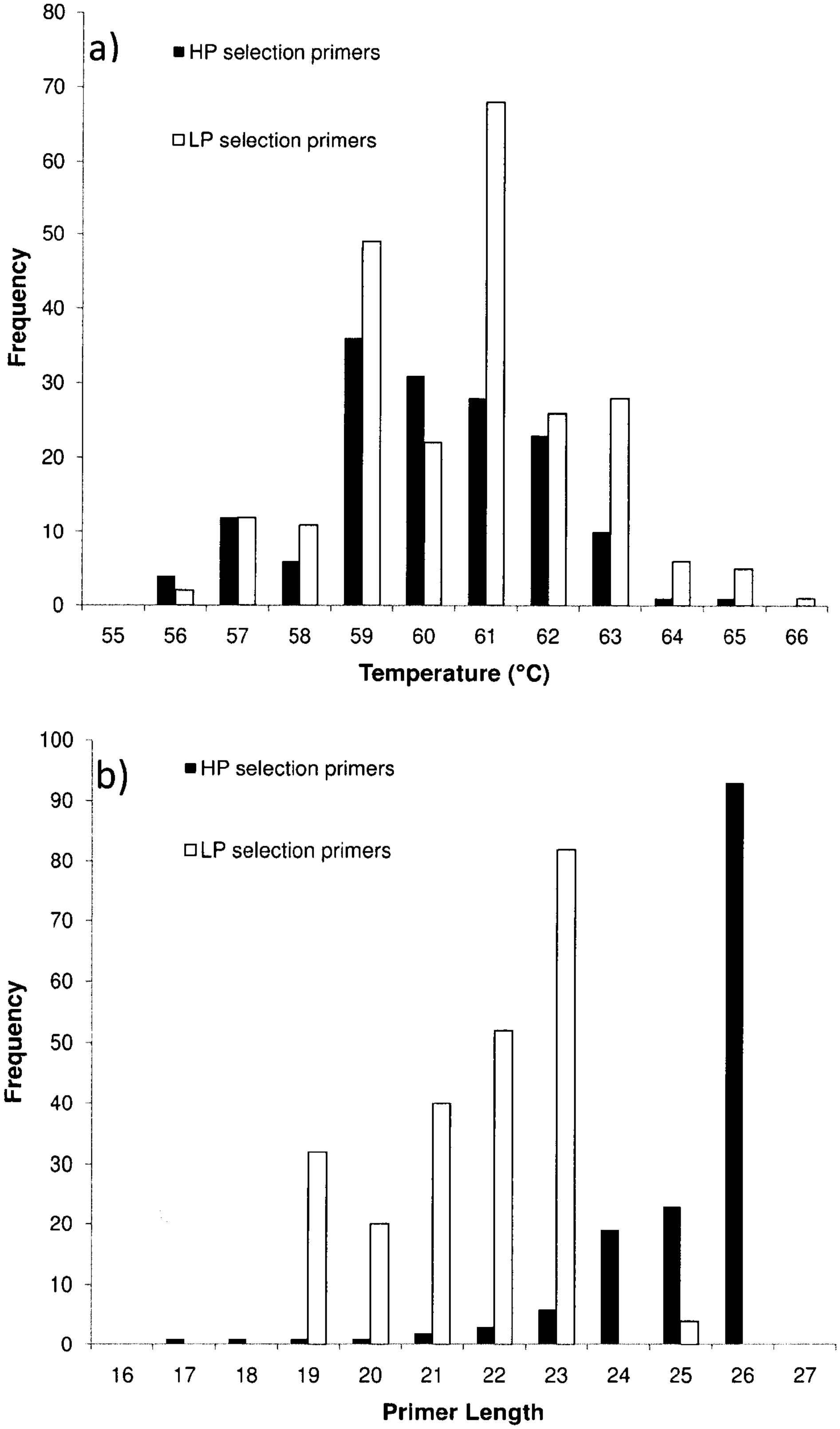
FIG. 9 shows the distribution of melting temperatures (a) and length (b) among the 382 selection primers. HP and LP signify primers detecting cleavage sites of high- and low-pathogenic viruses, respectively.

In February 2009, all unique cleavage site sequences from the Eastern hemisphere (or rather the whole world except the Americas) available at the NCBI database were compiled. It was found that 31 and 22 degenerate selection primers detecting high- and low-pathogenic cleavage sites, respectively, could account for all existing cleavage sites in the geographical region to which the study had been limited. This set of 53 degenerate primers covered in total 380 sequences. Subsequently, two more primers were added (see below). All primers were designed to, at least to some extent, cover the R↓G codons with their 3'-end and have a melting temperature close to 60° C. The adjustable parameters were the length of the primers and small shift relative to the cleavage site. The average melting temperature of the sets of high- and low-pathogenic primers were 59.7° C. (SD=1.7° C.; N=152) and 60.1° C. (SD=1.9° C.; N=230). The distribution of melting temperatures and primer lengths are given in FIG. 9. The concentrations of the selection and detection primers were 0.3 nM and 0.3 μM, respectively.

Figure 5:
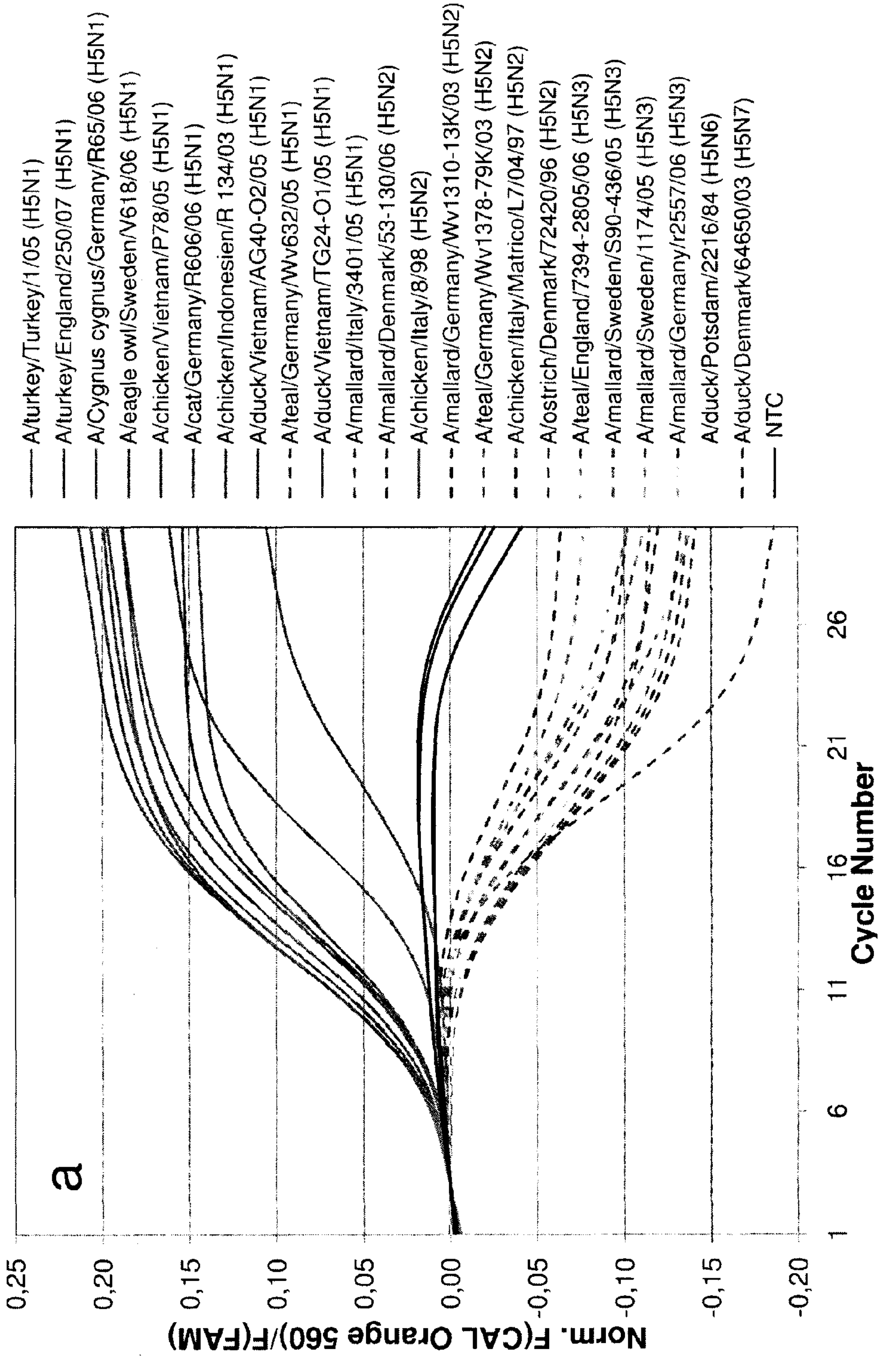
FIG. 5 shows the amplification curves displayed as the normalized ratio of the fluorescence signal in two channels ('JOE'/'FAM') obtained with Plexor® detection primers for H5 (a) and H7 (b) AIV pathotyping. The investigated AIV isolates are indicated. The pathogenicity of all isolates was previously known (Table 1 (H5) and Table 2 (H7)). High- and low-pathogenic isolates are shown with full and dashed lines, respectively. The assay is constructed to yield positive signal for high pathogenicity and negative signal for low pathogenicity and utilized 380 selection primers. The two isolates incorrectly pathotyped in (b) are:
A/mallard/Sweden/ 123455/08 (H7N7) and A/mallard/Sweden/ 100993/08 (H7N7).
Figure 5:
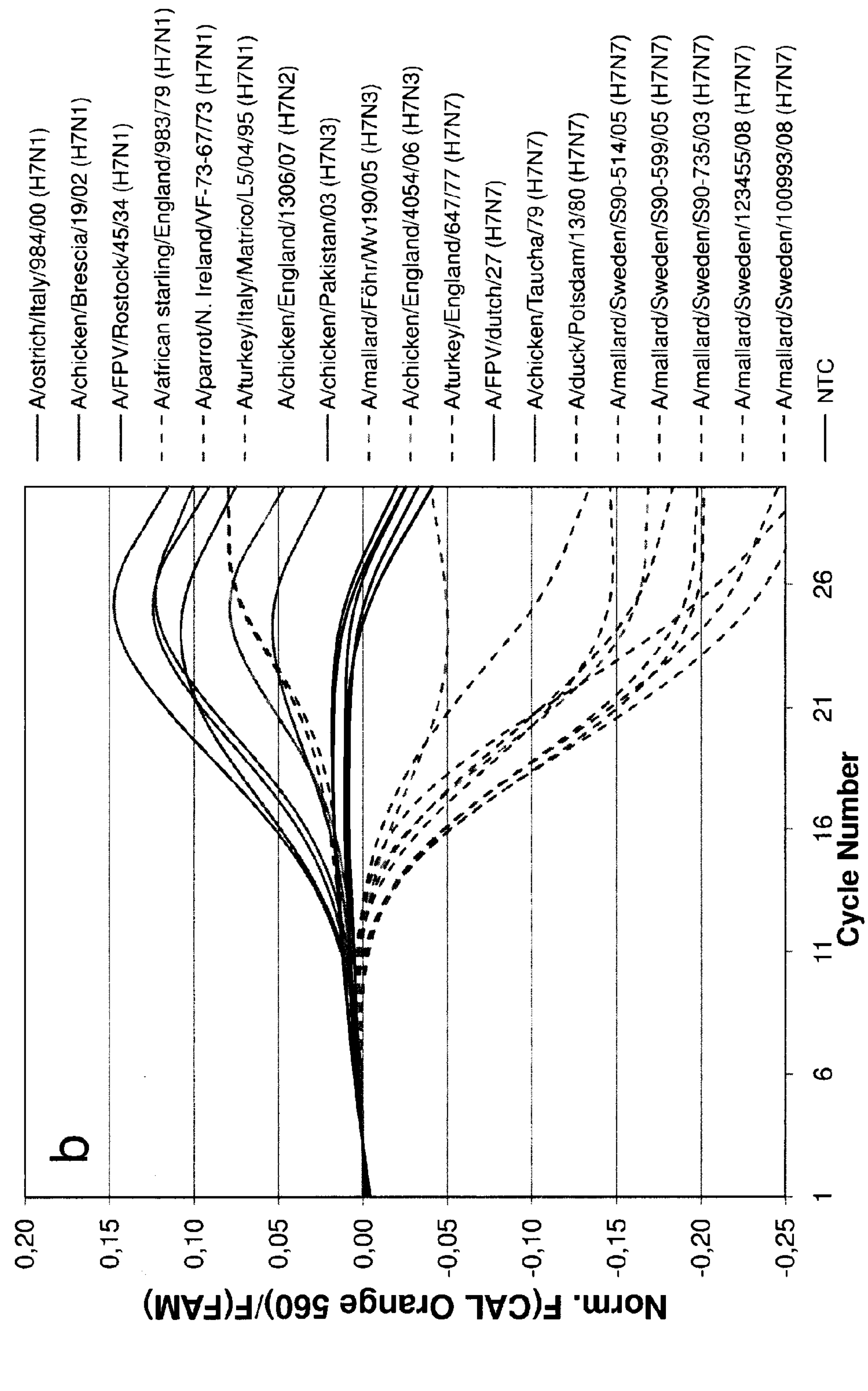
Figure 6:
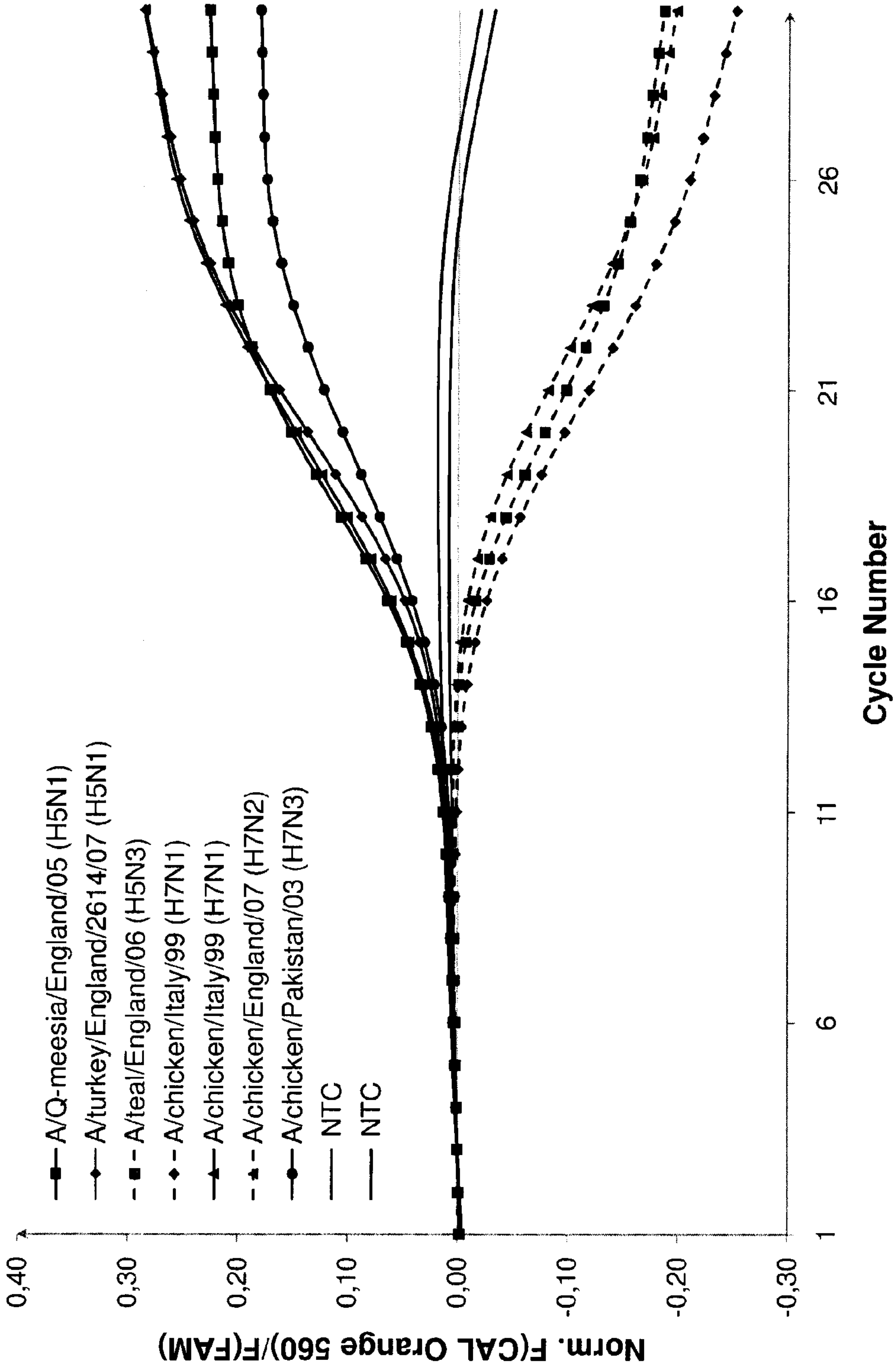
FIG. 6 shows the amplification curves displayed as the normalized ratio of the fluorescence signal in two channels ('JOE'/'FAM') obtained with Flexor® detection primers for pathotyping of the 2008 EU ring trial. The investigated AIV isolates are indicated in figure. The pathogenicity of all isolates was determined by cleavage site sequencing (Table 1 (H5) and Table 2 (H7)). High- and low-pathogenic isolates are shown with full and dashed lines, respectively. The assay is constructed to yield positive signal for high-pathogenicity and negative signal for low pathogenicity and utilized 380 selection primers.

To make the pathotyping strategy devised in the present investigation compatible with current procedures for avian influenza diagnostics in the EU, the primers used for H5 and H7 AIV detection and cleavage site sequencing by the EU central reference laboratories (CRLs)[7,18] were used for pre-amplification. Although the CRL PCR primers for detection of H5 and H7 subtypes are different, a single mastermix was used for all pathotyping reactions since the reverse primers from the two systems were co-added. The pathotype of all investigated isolates had been determined previously by nucleotide sequencing or was sequenced in the present study (Table 1). In FIG. 5 the amplification curves for isolates of high and low pathogenicity are shown with full and dashed lines, respectively. From FIG. 5*a* it is clear that all 23 H5 isolates are correctly pathotyped with the present assay while it is seen from FIG. 5*b* that two of the 19 H7 isolates are incorrectly pathotyped as high-pathogenic (A/mallard/123455/08 (H7N7) and A/mallard/100993/08 (H7N7)). However, these recent isolates with a novel cleavage site was not included in the initial design of the pathotyping assay. We will show later that a particular strength of the present assay strategy is a simple and straightforward extensibility to account for the emergence of novel isolates with previously unseen cleavage sites. To further challenge the pathotyping assay, the CRL distributed ring trial for 2008 were tested (FIG. 6). All pathotyping results obtained from the panel samples were consistent with cleavage site sequences (Table 1 and Table 2). Note that the virus A/chicken/Italy/99 (H7N1) exists in both a high- and a low-pathogenic variant. This corresponds to a pathogenicity conversion of this virus by mutations in the cleavage site region[19].

Figure 7:
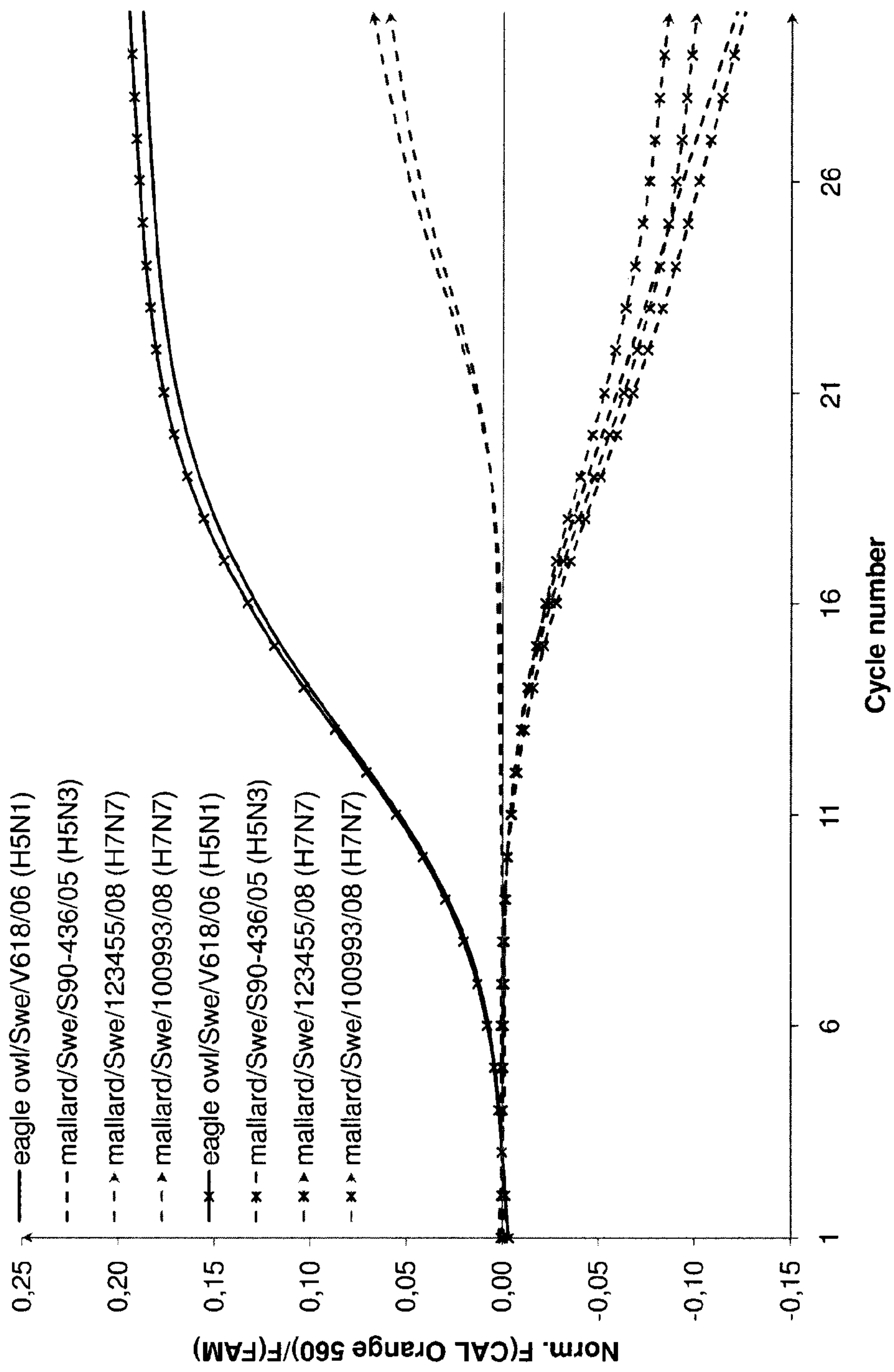
FIG. 7 shows the amplification curves displayed as the normalized ratio of the fluorescence signal in two channels ('JOE'/'FAM') obtained with Plexor® detection primers for pathotyping of the four AIV isolates indicated in the figure. Curves shown without and with crosses were obtained from experiments using a 380 and a 382 selection primer set, respectively. The pathogenicity of all isolates was determined by cleavage site sequencing (Table 1 (H5) and Table 2 (H7)). High-and low-pathogenic isolates are shown with full and dashed lines, respectively. The assay is constructed to yield positive signal for high-pathogenicity and negative signal for low pathogenicity.

Avian influenza virus genomes are extremely variable, in particular, the genes that are surface exposed. e.g., the haemagglutinin gene that largely accounts for pathogenicity. For this reason, it is important that a method for determination of pathogenicity is able to, in a simple way, account for new emerging virus variants. For determination of AIV pathogenicity, no such method has existed and the diagnostic practice has settled for DNA sequencing. In FIG. 7 four different isolates, including A/mallard/ 123455/08 (H7N7) and A/mallard/ 100993/08 (H7N7) incorrectly pathotyped in FIG. 5, are shown amplified with the original set of selection primers and an extended set including a selection primer accounting for the novel cleavage site carried by the 2008 H7N7 isolates (curves with crosses). It can be seen that the two H7N7 isolates (grey, arrowed curves) are selectively affected by the new primers and turn from positive signal (high-pathogenic) to negative signal (low-pathogenic) while the other two isolates remain virtually unaffected by the added primers. Thus, the assay can be very easily extended simply by adding new selection primers as required.

Figure 8:
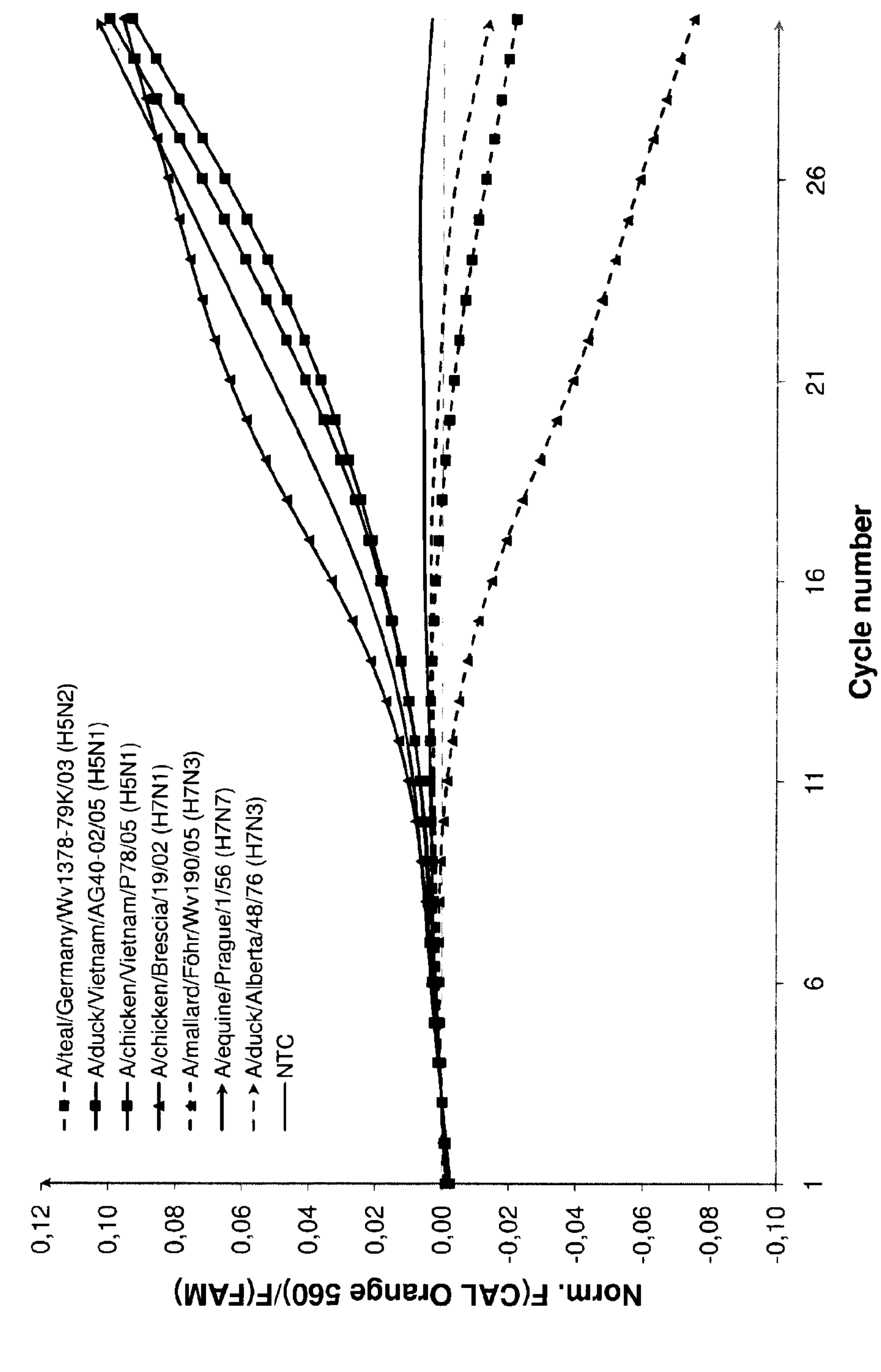
FIG. 8 shows the amplification curves displayed as the normalized ratio of the fluorescence signal in two channels ('JOE'/'FAM') obtained with Plexor® detection primers for pathotyping using the pan-HA primers[20] for pre-amplification. The experiments for pathotyping of the isolates indicated in the figure were run using the 382 selection primer set. The pathogenicity of all isolates was determined by cleavage site sequencing (Table 1 (H5) and Table 2 (H7)). High- and low-pathogenic isolates are shown with full and dashed lines, respectively. The assay is constructed to yield positive signal for high-pathogenicity and negative signal for low pathogenicity.

The pathotyping assay relies on successful pre-amplification. However, it was recently reported[20] that the recommended CRL primers[7] were unable to amplify for instance A/duck/Alberta/48/76 (H7N3) and we observed that these primers also were unable to amplify A/equine/Prague/ 1/56 (H7N7). New primers (pan-HA) were designed by Gall and colleagues to provide universal amplification for subsequent pathotyping by sequencing[20]. A further illustration of the flexibility of the present assay construct is provided by FIG. 8 where we instead of using the CRL primers have carried out the pre-amplification with the pan-HA primers and then, consequently, also used the pan-HA reverse primers as reverse primers in the pathotyping reaction, but otherwise kept all component of the pathotyping assay intact. It is seen in FIG. 8 that all isolates are correctly pathotyped including the A/duck/Alberta/48/76 (H7N3) and A/equine/Prague/ 1/56 (H7N7) isolates. The signal from A/duck/Alberta/48/76 (H7N3) appears quite weak since the closest match among the selection primers contains three mismatches. Since A/duck/Alberta/48/76 (H7N3) is a North American isolate, the sequence was not specifically accounted for in the design of the selection primers.

EXAMPLE 2

Extended Set of AIV Primers Covering All Isolates in the World

Viral RNA extraction. The viral RNA was obtained extracted from the National Veterinary Service Laboratory in Ames, Iowa, USA.

Reverse transcription and pre-amplification. Reverse transcription of the extracted RNA and DNA pre-amplification of the American H5 samples utilized the forward primer prfH5WH and the reverse primer prrH5WH, respectively (Table 4). The PCR systems were performed in 25 μl reaction volumes using the OneStep RT-PCR kit (Qiagen, Hilden, Germany) with primers at 1 μM concentrations and adding 2.5 μl of the extracted viral RNA in each reaction. The cycling condition was: 30 min reverse transcription at 50° C.; 15 min enzyme activation/deactivation at 96° C.; 40 cycles of: 96° C. for 10 sec, 58° C. for 30 sec, 68° C. for 30 sec; and a final extension step at 68° C. for 7 min. All amplifications were verified by agarose gel electrophoresis using pre-cast E-gel 2% with ethidium bromide (Invitrogen, Carlsbad, Calif.) and visualized under UV-light. The expected amplicons sizes was 300-320.

Primer design. Primers were designed as described above. The selection primer set was extended to include also cleavage sites from isolates from the western hemisphere (all cleavage sites in the whole world found in the ncbi database at the end of December 2009). The number of degenerate selection primers was 80 (Table 3) amounting to 468 unique primers. The detection primers were the same used in the original primer set (see above) and the reverse primers were prrH5EH, prrH5WH prrH7EH and prrH7WH. (Table 4)

Real-time PCR experiments. All selection primer concentrations were 0.3 nM and detection and reverse primer concentrations were 0.25 μM. Selection primers were obtained desalted and dissolved in water at 100 μM from Sigma-Aldrich and were used without further purification. Plexor® primers were obtained from Biosearch Technologies (Novato, Calif.) and the Plexor® qPCR System reagents from Promega (Madison, Wis.). All real-time PCR experiments were carried out on RotorGene 6000 instruments (Corbett Research, Sydney, Australia). The default FAM and JOE channels were used to excite and acquire the signal from the FAM and CAL Orange-560 labelled primers, respectively. Using the RotorGene 3000 standard software analysis tools the raw JOE channel signals were divided by the corresponding raw FAM channels signals and the resulting signals were baseline corrected by subtraction of the average value of the first five PCR cycles from all fluorescence difference values. The amplification was achieved by 30 cycles of: 10 sec at 95° C., 15 sec at 52° C. and 20 sec at 72° C., following an initial hold time of 3 min at 95° C.

Results

Figure 10:
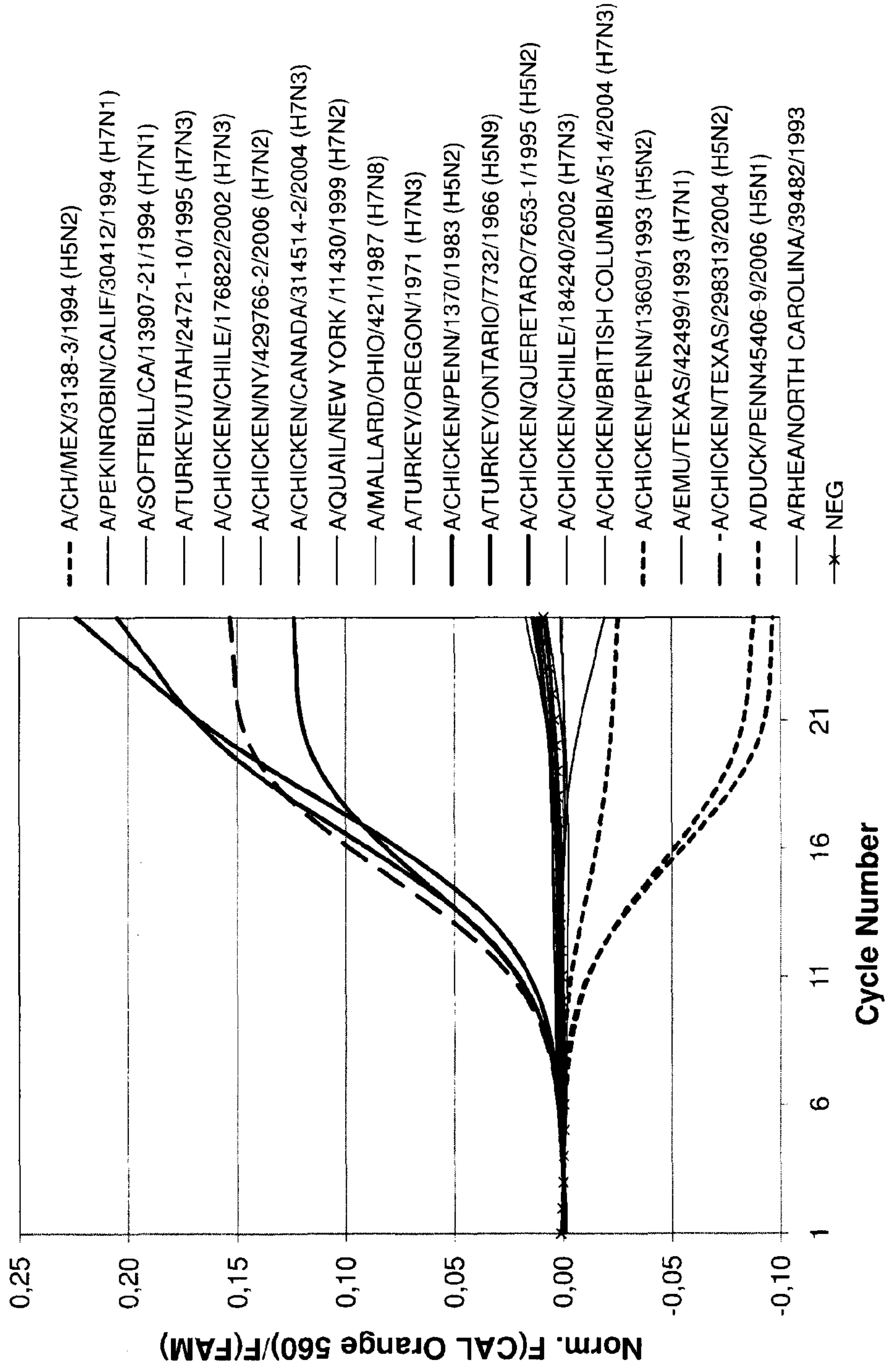
FIG. 10 shows the amplification curves obtained for american isolates displayed as the normalized ratio of the fluorescence signal in two channels ('JOE'/'FAM') obtained with Plexor® detection primers for pathotyping using an extended 468 selection primer set covering all cleavage site in the world derived from the ncbi sequence database in December 2009. The pathogenicity of all isolates was confirmed by standard methods. High- and low-pathogenic isolates are shown with full and short dashed lines, respectively. One isolate is displayed with long dash and is low pathogenic but carries a cleavage site typical for high pathogenic viruses. This isolate is also detected as highly pathogenic by the design of the method. The assay is constructed to yield positive signal for high pathogenicity and negative signal for low pathogenicity. Samples with thin lines are negative and where American H7-types. The pre-amplification primers designed are H7 and H5 specific and in this Figure the H5-specific primers where used.

It can be seen from FIG. 10 that H7 isolates (thin lines in FIG. 10) did not give significant signals and behaved as the negative control (thin line with cross). Highly pathogenic American H5 isolates (thick lines; full) and a low pathogenic isolate with cleavage site signifying highly pathogenic isolates (thick line; long dash) gave positive F(JOE)/F(FAM) signals while low pathogenic American H5 isolates gave negative signals (think line; short dash).

EXAMPLE 3

NDV Pathotyping

RNA Extraction and Pre-Amplification

RNA was extracted from the allantoic fluids of the NDV infected embryonated eggs by using MagAttract Virus Mini M48 kit (Qiagen, Hilden, Germany) following the manufacturer's instructions with the Magnatrix 8000 extraction robot (Magnetic Biosolutions, Sweden). RNA was recovered in 70 μl of nuclease-free water and either used immediately or stored at −80° C.

OneStep RT-PCR kit (Qiagen, Hilden, Germany) were used for RNA transcription and pre-amplification for all NDV strains, using NDV P1F and P2R sequencing primers (Table 7). The RT-PCR were performed in 250 reaction volume containing 0.6 μM of each primers and 2.5 μl of extracted RNA. The Cycling profile was 60° C., 30 min; 95.C, 15 min; and 40 cycles of (94° C., 20 sec; 60° C., 15 sec; 72° C., 15 sec) and a final extension 72° C. for 10 min. PCR products were detected by 2% agarose gel electrophoresis after staining with ethidium-bromide (Invitrogen, Carlsbad, Calif.) and visualized under UV-light. The expected amplicon product size was 362 bp.

Primer Design

NCBI search for nucleotide sequences of NDV Fusion genes (F) from March 2010 gave a result of 2757 sequences by using a computer program CLC Main Workbench 5 (CLC bio A/S, Aarhus, Denmark). Due to the huge number of NDV sequences, they were divided into 5 groups according the years of registration in the NCBI GenBank, the sequences were aligned separately by the CLC Main Workbench 5. The size of the sequences were reduced to 30-mers covering the cleavage site of the F gene which include residue 117 of the N terminus of the F1 protein which is phenylalanine (F) as a marker for virulence for the mesogenic and velogenic strains (R▼F) and leusine (L) as a marker for low virulence for lenogenic strains (R▼L). Redundant sequences were removed by using Jalview 2.6. 251 unique cleavage site remained. That were accounted for by 68 primers (Table 6). The Plexor® primers for detection of high- and low pathogenic cleavage sites, have the same sequence as the overhang part of the corresponding bipartite selection primers but are labeled at the 5'-end with FAM and CAL Orange-560, respectively. The reverse primer used in the two-level pathotyping assay are the same reverse primer of the pre-amplification systems used.

Real-Time PCR Experiments

Selection primers were obtained desalted and dissolved in water at 100 μM (Sigma-Aldrich, Haverhill, UK. All selection primer concentrations were 0.3 nM and detection and reverse primer concentrations were 0.3 μM. Plexor® primers were obtained from Biosearch Technologies (Novato, Calif.) and the Plexor® qPCR System reagents from Promega (Madison, Wis.). All real-time PCR experiments were carried out on RotorGene 3000 instruments (Corbett Research, Sydney, Australia). The default FAM and JOE channels were used to excite and acquire the signal from the FAM and CAL Orange-560 labelled primers, respectively. The amplification was achieved by 30 cycles of: 10 sec at 95° C., 15 sec at 55° C. and 20 sec at 72° C., following an initial hold time of 3 min at 95° C. in a 25 pl reaction volume.

DNA Sequencing

Many samples that had been used in the pathotyping are without identity for this reason PCR-products from the pre-amplification were sequenced. Big Dye Terminator v3.1 cycle sequencing kit (Applied Biosystems, Foster City, Calif.) were used. Reaction volumes were 20 μl with 1.8 μl (2 pmol) of each primers, 2 μl of the big dye mix and 2 μl of the PCR-product. The cycling condition were: 25 cycles of 96° C. for 15 sec, 50° C. for 10 sec and 60° C. for 2 min. The products were purified by using Montage SEQ96 Sequencing Reaction Cleanup Kit (Millipore Corporation, Billerica, Mass.) and subsequently analyzed on an ABI Prism 3130x1 capillary sequencer (Applied Biosystems, Foster City, Calif.). Sequence data were analyzed by CLC Main Workbench 5.

Results

Figure 11:
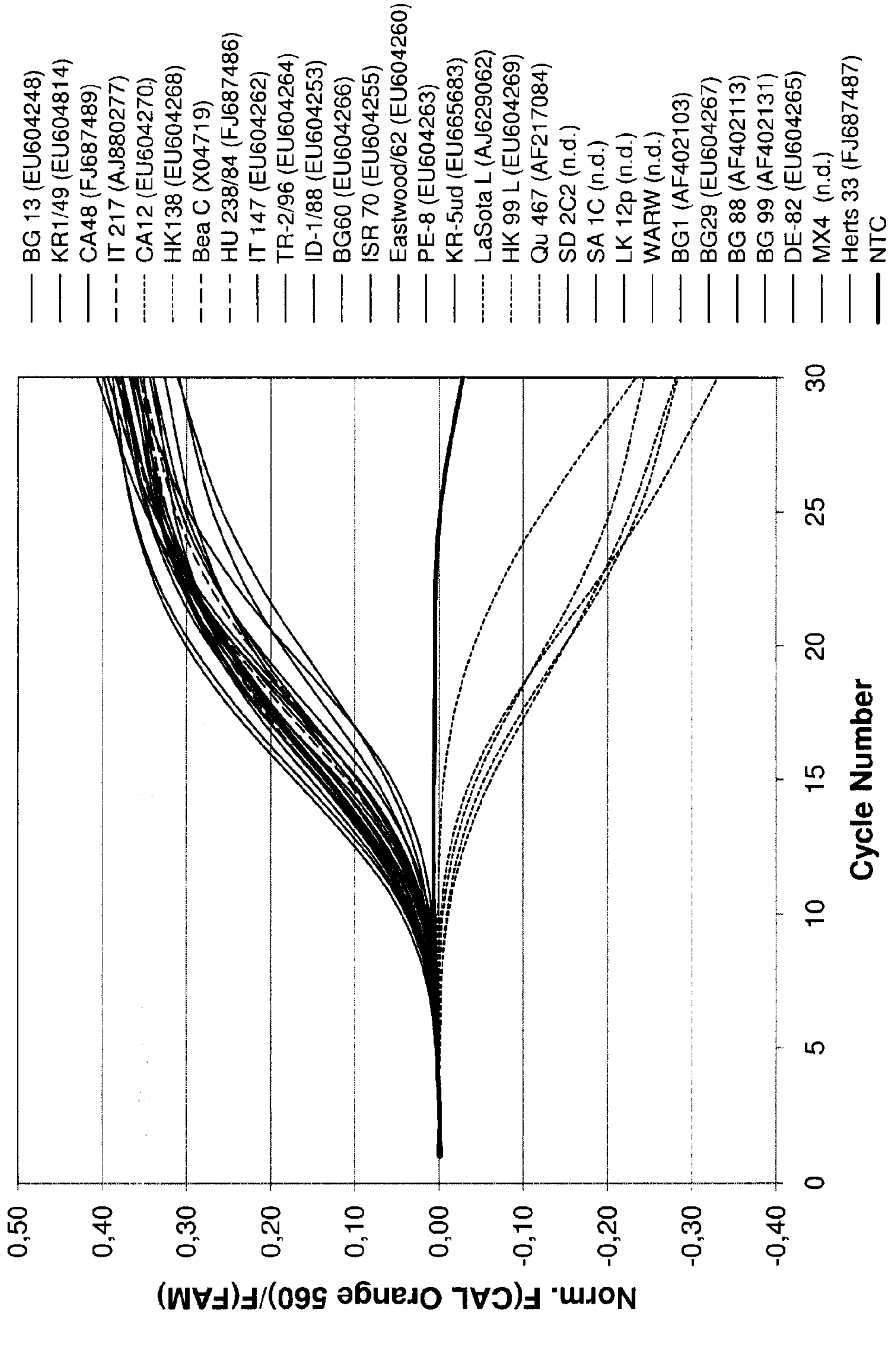
FIG. 11 shows the amplification curves displayed as the normalized ratio of the fluorescence signal in two channels (VOETFAM) obtained with Plexor® detection primers for pathotyping of Newcastle Disease virus (NDV). Mesogenic (long dash) and velogenic (full line) strains are considered highly pathogenic and lentogenic (short dash) isolates are low pathogenic. The experiments for pathotyping of the isolates indicated in the figure were run using the 252 selection primer set. The pathogenicity of 25 isolates was previously known in the literature, the other 5 isolates (SD2C2, SA1C, LK2p, WARW and MX4) the cleavage sites were sequenced. The assay is constructed to yield positive signal for high pathogenicity and negative signal for low pathogenicity.

In FIG. 11 the amplification curves are displayed as the normalized ratio of the fluorescence signal in two channels ('JOE'/'FAM') obtained with Plexor® detection primers for pathotyping of Newcastle Disease virus (NDV). Mesogenic (long dash) and velogenic (full line) strains are considered highly pathogenic and lentogenic (short dash) isolates are low pathogenic. The experiments for pathotyping of the isolates indicated in the figure were run using the 252 selection primer set. The pathogenicity of 25 isolates was previously known in the literature, the other 5 isolates (SD2C2, SA1C, LK2p, WARW and MX4) the cleavage sites were sequenced. The assay is constructed to yield positive signal for high pathogenicity and negative signal for low pathogenicity. All 30 isolates were correctly pathotyped.

TABLE 1

Cleavage sites of investigated H5 AIV isolates

| Name | Cleavage site sequence[a] | ST[b] | PT[b] | Origin |
|---|---|---|---|---|
| A/turkey/England/250/07 | agccctcaaggagagagaagaagaaaaaagaga↓gga | H5N1 | HP | VLA[c] |
| A/turkey/Turkey/1/05 | agccctcaaggagagagaagaagaaaaaagaga↓gga | H5N1 | HP | VLA |
| A/mallard/Italy/3401/05 | ggactcaggaatgttcctcaaagagaaacaaga↓ggg | H5N1 | LP | VLA |
| A/eagle owl/Sweden/V618/06 | agccctcaaggagagagaagaagaaaaaagaga↓gga | H5N1 | HP | SVA[c] |
| A/Cygnus cygnus/Germany/R65/06 | agccctcaaggagagagaagaagaaaaaagaga↓gga | H5N1 | HP | FLI[c] |
| A/cat/Germany/R606/06 | agccctcaaggagagagaagaagaaaaaagaga↓gga | H5N1 | HP | FLI |
| A/chicken/Indonesien/R 134/03 | agccctcaaagagagagaagaagaaaaaagaga↓gga | H5N1 | HP | FLI |
| A/teal/Germany/Wv632/05 | ggacccaggaatgtccctcaaaaagaaacaaga↓gga | H5N1 | LP | FLI |
| A/duck/Vietnam/TG24-01/05 | aatagccctcaaagagagagaaggaaaaagaga↓gga | H5N1 | HP | FLI |
| A/duck/Vietnam/AG40-02/05 | aatagccctcaaagagagagaagaaaaaagaga↓gga | H5N1 | HP | FLI |
| A/chicken/Vietnam/P78/05 | aatagccctcaaagagagagaagaagaaagaga↓gga | H5N1 | HP | FLI |
| A/ostrich/Denmark/72420/96 | Unknown | H5N2 | LP | SVA |
| A/chicken/Italy/Matrico/L7/04/97 | ggactcaggaatgtccctcagagagagacgaga↓gga | H5N2 | LP | IZS-Ve[c] |

TABLE 1-continued

Cleavage sites of investigated H5 AIV isolates

| Name | Cleavage site sequence[a] | ST[b] | PT[b] | Origin |
|---|---|---|---|---|
| A/mallard/Denmark/53-130/06[d] | Unknown | H5N2 | LP | VLA |
| A/chicken/Italy/8/98 | aggaatgtccctcaaagaagaagaaaaaaaaga↓gga | H5N2 | HP | FLI |
| A/mallard/Germany/Wv1310-13K/03 | cagagagaaacaaga↓gga[d] | H5N2 | LP | FLI |
| A/teal/Germany/Wv1378-79K/03 | Unknown | H5N2 | LP | FLI |
| A/teal/England/7394-2805/06 | Unknown | H5N3 | LP | SVA |
| A/mallard/Sweden/S90-436/05 | Unknown | H5N3 | LP | SVA |
| A/mallard/Sweden/1174/05 | ggactcaggaatgtccctcagagagagacgaga↓gga | H5N3 | LP | SVA |
| A/mallard/Germany/r2557/06[e] | Unknown | H5N3 | LP | VLA |
| A/duck/Potsdam/2216/84 | gggcttaggaatgttcctcaaagagagacaaga↓ggt | H5N6 | LP | FLI |
| A/duck/Denmark/64650/03 | ggactcaggaatgtccctcaaaaagaaacaaga↓gga | H5N7 | LP | SVA |
| EU Ring Test 2008[f] | | | | |
| A/teal/England/06 | ggactcaggaatgtccctcaaaaagaaacaaga↓gga | H5N3 | LP | VLA |
| A/turkey/England/2614/07 | agccctcaaggggagagaagaagaaaaaagaga↓gga | H5N1 | HP | VLA |
| A/Q-meesia/England/05 | aatagtcctccaagagaaagaagaagaaaaaga↓gga | H5N1 | HP | VLA |

[a]From NCBI.
[b]ST, subtype; PT, pathotype.
[c]VLA, Veterinary Laboratory Agency, UK; SVA, National Veterinary Institute, Sweden; FLI, Freidrich-Löffler Institute, Germany; IZS-Ve, Istituto Zooprofilattico Sperimentale Delle Venezie, Italy.
[d]From Fereidouni, S. R. et al. *J. Virol Methods* 154, 14-19 (2008)..
[e]From the 2009 AIV Epizone panel.
[f]Sequenced at SVA, Sweden.

TABLE 2

Cleavage sites of investigated H7 AIV isolates

| Name | Cleavage site sequence[a] | ST[b] | PT[b] | Origin |
|---|---|---|---|---|
| A/african starling/England/983/79 | atgaagaacgttcccgaaattccaaaaggaaga↓ggc | H7N1 | LP | VLA[c] |
| A/turkey/Italy/Matrico/L5/04/95 | atgaagaatgttcccgaaattccaaagggaaga↓ggc | H7N1 | LP | IZS-Ve[c] |
| A/parrot/N. Ireland/VF-73-67/73 | atgaagaacgttcctgaaattccaaaaggaaga↓ggc | H7N1 | LP | AHS[c] |
| A/ostrich/Italy/984/00[d] | cccgaaattccaaaaggatcgcgtgtgaggaga↓ggc | H7N1 | HP | VLA |
| A/chicken/Brescia/19/02 | gttcccgaacttcccaaaaaaagaagaaaaaga↓ggc | H7N1 | HP | FLI[c] |
| A/FPV/Rostock/45/34 | gttcccgaaccttccaaaaaaaggaaaaaaaga↓ggc | H7N1 | HP | FLI |
| A/chicken/England/1306/07[d] | atgaagaatgttcccgaaatcccaaagggaaga↓ggc | H7N2 | LP | VLA |
| A/chicken/England/4054/06 | atgaagaatgttcccgaaatcccaaagggaaga↓ggc | H7N3 | LP | VLA |
| A/mallard/Föhr/Wv190/05 (H7N3) | Unknown | H7N3 | LP | FLI |
| A/duck/Alberta/48/76 (H7N3) | atgagaaatgtcccagaaaatccaaagaccaga↓gga | H7N3 | LP | FLI |
| A/turkey/England/647/77 | atgaagaacgttcctgaaattccaaaagggaga↓ggc | H7N7 | LP | VLA |
| A/mallard/Sweden/S90-514/05 | atgaagaatgttcccgaaatcccaaagggaaga↓ggc | H7N7 | LP | SVA[c] |
| A/mallard/Sweden/S90-599/05 | atgaagaatgttcccgaaatcccaaagggaaga↓ggc | H7N7 | LP | SVA |
| A/mallard/Sweden/S90-735/03 | atgaagaatgttcccgaaatcccaaagggaaga↓ggc | H7N7 | LP | SVA |
| A/mallard/Sweden/123455/08 | Unknown | H7N7 | LP | SVA |
| A/mallard/Sweden/10093/08 | atgaagaatgttcctgaaatcccaaagaaaaga↓ggc | H7N7 | LP | SVA |
| A/duck/Potsdam/13/80 | Unknown | H7N7 | LP | FLI |

TABLE 2-continued

Cleavage sites of investigated H7 AIV isolates

| Name | Cleavage site sequence[a] | ST[b] | PT[b] | Origin |
|---|---|---|---|---|
| A/FPV/dutch/27 | gttcccgaactccccaaaaaaagaagaaaaaga↓ggc | H7N7 | HP | FLI |
| A/chicken/Taucha/79 | Unknown | H7N7 | HP | FLI |
| A/equine/Prague/1/56 | aaacaactaactcatcacatgcgcaaaaaaaga↓ggt | H7N7 | HP | FLI |
| EU Ring test 2008[e] | | | | |
| A/chicken/Pakistan/03 | aacgttcctgaaactccaaaaagaagaaaaaga↓ggc | H7N3 | HP | VLA |
| A/chicken/Italy/99 (H7N1) | atgaagaatgttcccgaaattccaaagggaaga↓ggc | H7N1 | LP | VLA |
| A/chicken/England/07 (H7N2) | atgaagaatgttcccgaaatcccaaagggaaga↓ggc | H7N2 | LP | VLA |
| A/chicken/Italy/99 (H7N1) | cccgaaattccaaaaggatcgcgtgtgaggaga↓ggc | H7N1 | HP | VLA |

[a]From NCBI.
[b]ST, subtype; PT, pathotype.
[c]VLA, Veterinary Laboratory Agency, UK; SVA, National Veterinary Institute, Sweden; FLI, Freidrich-Löffler Institute, Germany; IZS-Ve, Istituto Zooprofilattico Sperimentale Delle Venezie, Italy;
[d]From the 2009 AIV Epizone panel.
[e]Sequenced at SVA, Sweden.

TABLE 3

Selection primers Avian Influenza Virus

| Designation | SEQ ID NO | Sequence |
|---|---|---|
| fsHP01 | 1 | CGGGAACTATCACCAAACAACACCCCGCAAGGAGARAGAARAAGAAAAAAGAG |
| fsHP02 | 2 | CGGGAACTATCACCAAACAACACCCCGAAGGGGAGAGAAGAAGAAAAAAGAG |
| fsHP03 | 3 | CGGGAACTATCACCAAACAACACCCCGCCCTCAAAGAAAAAGAAAAACAAGAG |
| fsHP28 | 4 | CGGGAACTATCACCAAACAACACCCCGCAAAGAGARAGAAGAARRAAAAGARG |
| fsHP29 | 5 | CGGGAACTATCACCAAACAACACCCCGAAGAGARAGAAGAARRAAGCGARG |
| fsHP06 | 6 | CGGGAACTATCACCAAACAACACCCCGGTCCCTCAAAGGAAGAAAAGAG |
| fsHP30 | 7 | CGGGAACTATCACCAAACAACACCCCGGAGAKARAAGAAGAAAAAAGMGAGG |
| fsHP31 | 8 | CGGGAACTATCACCAAACAACACCCCGGAGAKARAAGAAGAAAAAAGAGRGG |
| fsHP32 | 9 | CGGGAACTATCACCAAACAACACCCCGRGAGAKARAAGAAGAAARAARAGAGG |
| fsHP33 | 10 | CGGGAACTATCACCAAACAACACCCCGRGAGAKARAAGAAGAAAAARGARAGG |
| fsHP37 | 11 | CGGGAACTATCACCAAACAACACCCCGGGAGAGAGAAGAAGAAAAAAGAGAGG |
| fsHP38 | 12 | CGGGAACTATCACCAAACAACACCCCGCCCTCAAAGAAGAAAAAAAAGAGG |
| fsHP08 | 13 | CGGGAACTATCACCAAACAACACCCCGCCTCAAAGAARAAGAAAAAARAGAGG |
| fsHP09 | 14 | CGGGAACTATCACCAAACAACACCCCGGGATCGCGTGTGAGGAG |
| fsHP10 | 15 | CGGGAACTATCACCAAACAACACCCCGCCAAAAAAAGGAAAAAAAGAGG |
| fsHP11 | 16 | CGGGAACTATCACCAAACAACACCCCGGATCGCGSGTGAGGAG |
| fsHP13 | 17 | CGGGAACTATCACCAAACAACACCCCGCCAAAGAGGAGGAGGAGAGG |
| fsHP14 | 18 | CGGGAACTATCACCAAACAACACCCCGCCAAAAAAGAGGAAAAAGAGAGG |
| fsHP15 | 19 | CGGGAACTATCACCAAACAACACCCCGTTCCAAAAAGGAAAAAGAGAGG |
| fsHP34 | 20 | CGGGAACTATCACCAAACAACACCCCGAAACTCCAAAAAGAAGAARMAGAGG |
| fsHP17 | 21 | CGGGAACTATCACCAAACAACACCCCGCCAAAAAAGAAAAAGAAAAAGAGAGG |
| fsHP35 | 22 | CGGGAACTATCACCAAACAACACCCCGCCCAAAAAAAGAAGAAARAGAGG |
| fsHP19 | 23 | CGGGAACTATCACCAAACAACACCCCGGAAATTCCAAAAAAGAAAAAGAGAGG |

TABLE 3-continued

Selection primers Avian Influenza Virus

| Designation | SEQ ID NO | Sequence |
|---|---|---|
| fsHP21 | 24 | CGGGAACTATCACCAAACAACACCCCGAGAGAGGGAGGAAGAAGAAAAAGAGG |
| fsHP22 | 25 | CGGGAACTATCACCAAACAACACCCCGAAAGAGAGAGAAGGAAAAAGAGAGG |
| fsHP23 | 26 | CGGGAACTATCACCAAACAACACCCCGAAAAAAGAAAAAGAAAAAGAGGCC |
| fsHP26 | 27 | CGGGAACTATCACCAAACAACACCCCGCCCGAGAARGAGAAAGAGAGG |
| fsHP39 | 28 | CGGGAACTATCACCAAACAACACCCCGTTCCAAAAAGAGAACAAAAAGAGG |
| fsHP40 | 29 | CGGGAACTATCACCAAACAACACCCCGAAATCCCAAAGAGAAAGAAAAGAGG |
| fsHP41 | 30 | CGGGAACTATCACCAAACAACACCCCGCCCRAAGAAGAGAGAGAAGAGAG |
| fsHP42 | 31 | CGGGAACTATCACCAAACAACACCCCGGCGCAGGCAGAAAAGAGG |
| fsHP43 | 32 | CGGGAACTATCACCAAACAACACCCCGACATGCGCAAAAAAAGAGG |
| fsHP44 | 62 | CGGGAACTATCACCAAACAACACCCCGTTCCCCAAAGAGAAAAAAGAGG |
| fsHP45 | 63 | CGGGAACTATCACCAAACAACACCCCGCCCCAAAGGAAAAAAAGAGG |
| fsHP46 | 64 | CGGGAACTATCACCAAACAACACCCCGGGRGGAAGAAGRAGAAAAAGAGG |
| fsHP47 | 65 | CGGGAACTATCACCAAACAACACCCCGCCCCGACCCAGAAGAGG |
| fsHP48 | 66 | CGGGAACTATCACCAAACAACACCCCGGCCCCAGAAGAAAAAGAGAGG |
| fsHP49 | 67 | CGGGAACTATCACCAAACAACACCCCGGTGCMTCAGARGAARAAGAGAGG |
| fsHP50 | 68 | CGGGAACTATCACCAAACAACACCCCGGTACCCCAAAGGAAAAAAAGAGG |
| fsHP51 | 69 | CGGGAACTATCACCAAACAACACCCCGAGAAAAAGAAAAAGAAAAACAAGAGG |
| fsHP52 | 70 | CGGGAACTATCACCAAACAACACCCCGMAKAAACGGATGACCAGAGG |
| fsHP53 | 71 | CGGGAACTATCACCAAACAACACCCCGGGAAACGRATGACCAGAGG |
| fsHP54 | 72 | CGGGAACTATCACCAAACAACACCCCGGGTGCAGARAAACCAGAGG |
| fsHP55 | 73 | CGGGAACTATCACCAAACAACACCCCGAAATTCCAAAAAGAAGAAGGGG |
| fsLP14 | 33 | CGGGACAACAAACCACTATCAACCCCGATYCCTCARARAGRAACAARAGG |
| fsLP18 | 34 | CGGGACAACAAACCACTATCAACCCCGTYCCTCARARAGRAACAARAGG |
| fsLP19 | 35 | CGGGACAACAAACCACTATCAACCCCGGTYCCTCARARAGAGACAARAGG |
| fsLP21 | 36 | CGGGACAACAAACCACTATCAACCCCGGTYCCTCARARAGRTACAARAGG |
| fsLP26 | 37 | CGGGACAACAAACCACTATCAACCCCGCCCTCAGAGAGAGACGAGAGG |
| fsLP02 | 38 | CGGGACAACAAACCACTATCAACCCCGCCCTCAACGAGAAACAAGAGG |
| fsLP03 | 39 | CGGGACAACAAACCACTATCAACCCCGYCCTCAAARGGAGACAAGAGG |
| fsLP22 | 40 | CGGGACAACAAACCACTATCAACCCCGCCTGAAAYTCCAAAAGRAAGG |
| fsLP23 | 41 | CGGGACAACAAACCACTATCAACCCCGCCTGAAAYTCCAAAAGGAAAAGG |
| fsLP05 | 42 | CGGGACAACAAACCACTATCAACCCCGYGAAATTCCAAARGGAAGAGG |
| fsLP07 | 43 | CGGGACAACAAACCACTATCAACCCCGCGAARTYCCAAARGGRAGAG |
| fsLP08 | 44 | CGGGACAACAAACCACTATCAACCCCGGAAAYCCCAAAKGGAAGAGG |
| fsLP10 | 45 | CGGGACAACAAACCACTATCAACCCCGCYGAARTCCCRAAKGGAAR |
| fsLP24 | 46 | CGGGACAACAAACCACTATCAACCCCGCCTGARAYTCCAAAAGGRAGAG |
| fsLP25 | 47 | CGGGACAACAAACCACTATCAACCCCGCTGARAYTCCAAAGGGRAGAG |
| fsLP12 | 48 | CGGGACAACAAACCACTATCAACCCCGCTGAAATTCCAAAAGGAAGAGG |
| fsLP13 | 49 | CGGGACAACAAACCACTATCAACCCCGAATGTYCCTCAAARAGAAACAAGAG |

TABLE 3-continued

| Selection primers Avian Influenza Virus | | |
|---|---|---|
| Designation | SEQ ID NO | Sequence |
| fsLP27 | 50 | CGGGACAACAAACCACTATCAACCCCGGTTCCTCAAAGAGACACAAGGG |
| fsLP29 | 52 | CGGGACAACAAACCACTATCAACCCCGTCCTCAAAGGGAAACAAGAGG |
| fsLP30 | 53 | CGGGACAACAAACCACTATCAACCCCGTGGAGTCCCAAGAAAAAGAGG |
| fsLP31 | 54 | CGGGACAACAAACCACTATCAACCCCGCGGAAAATCCRAAGAMKAGAGG |
| fsLP32 | 55 | CGGGACAACAAACCACTATCAACCCCGCTGAAATCCCAAAGAAAAGAGG |
| fsLP33 | 74 | CGGGACAACAAACCACTATCAACCCCGAGAGAACCCAAAGACCAGAGG |
| fsLP34 | 75 | CGGGACAACAAACCACTATCAACCCCGTACCAGAAACAGATGACCAGAGG |
| fsLP35 | 76 | CGGGACAACAAACCACTATCAACCCCGCAGAGAAWCCAAAGACCAGAGG |
| fsLP36 | 77 | CGGGACAACAAACCACTATCAACCCCGAGAGAABCCMAAGACCAGRGG |
| fsLP37 | 78 | CGGGACAACAAACCACTATCAACCCCGGARARCCCMAARACCAGAGG |
| fsLP38 | 79 | CGGGACAACAAACCACTATCAACCCCGCAGAAAATCCAAAAACCAGAGG |
| fsLP39 | 80 | CGGGACAACAAACCACTATCAACCCCGARAAWCCAAAGCCCAGAGG |
| fsLP40 | 81 | CGGGACAACAAACCACTATCAACCCCGAGAGAAACCAAARCCMAGAGG |
| fsLP41 | 82 | CGGGACAACAAACCACTATCAACCCCGAGAAAAACCAAAGACAAGGGG |
| fsLP42 | 83 | CGGGACAACAAACCACTATCAACCCCGCCAGAAAAACCAAAGACAAGAGG |
| fsLP43 | 84 | CGGGACAACAAACCACTATCAACCCCGCAGAGAATCCAAAGACTAGGGG |
| fsLP44 | 85 | CGGGACAACAAACCACTATCAACCCCGCCCCARARAGRAACAARAGG |
| fsLP45 | 86 | CGGGACAACAAACCACTATCAACCCCGCCCARARAGRAACAARGGG |
| fsLP46 | 87 | CGGGACAACAAACCACTATCAACCCCGTACCCCAAAGAAAAACAAGAGG |

TABLE 4

| Pre-amplification primers Avian Influenza Virus (H5 and H7 specific) | | |
|---|---|---|
| Designation | SEQ ID NO | Sequence |
| prfH5EH | 88 | RAAYTTYATTGCTCCAGAAWATGCATAC |
| prrH5EH/H5-kha-3 | 59 | TACCAACCGTCTACCATKCCYTG |
| prfH5WH | 89 | TTTATAGCTCCYGAATATGCRTACAA |
| prrH5WH | 90 | TACCAYCCRTCHACCATTCCTT |
| prfH7EH | 91 | ATGYCCGAGATATGTWAARCA |
| prrH7EH | 92 | TTTGTAATCTGCHGCAGTYC |

TABLE 4-continued

| Pre-amplification primers Avian Influenza Virus (H5 and H7 specific) | | |
|---|---|---|
| Designation | SEQ ID NO | Sequence |
| GK7.4 | 57 | TTTGTAATCTGCAGCAGTTC |
| prfH7WH.1 | 93 | GCCCTCGRTATGTCARACA |
| prfH7WH.2 | 94 | CCCTCGRTATGTCARGCA |
| prrH7WH | 95 | TTTGTARTCAGCTGCAGTYC |

Designation system: pr = pre-amplification; f = forward; r = reverse; H5/H7 = specificity; EH = Eastern Hemisphere, WH = Western Hemisphere GK7.4 is an alternative to prrH7EH

TABLE 5

| Detection primers Avian Influenza Virus | | |
|---|---|---|
| Designation | SEQ ID NO | Sequence |
| fdHP | 60 | Fam-isoC-CGGGAACTATCACCAAACAACACCCCG |
| fdLP | 61 | CAL orange 560-isoC-CGGGACAACAAACCACTATCAACCCCG |

TABLE 6

| SEQ ID NO | Designation | Selection primers for Newcastle Disease Virus Sequence |
|---|---|---|
| | | Primer name for Mesogenic and velogenic NDV strains |
| 96 | FSM04.5 | CGGGAACTATCACCAAACAACACCCCGGAAAGGAGACAGAAACGCTTTATA |
| 97 | FSM04.16 | CGGGAACTATCACCAAACAACACCCCGGGAAGGAGGCAGAGACGCTTTATA |
| 98 | FSV01 | CGGGAACTATCACCAAACAACACCCCGAAGGAGACAGAAACGCTTCGTA |
| 99 | FSV02.3 | CGGGAACTATCACCAAACAACACCCCGGAGAAGACGGAAACGCTTTATA |
| 100 | FSV02.8 | CGGGAACTATCACCAAACAACACCCCGGAGGAGACGGAAGCGCTTTATA |
| 101 | FSV03.2 | CGGGAACTATCACCAAACAACACCCCGGAAGGAGACAGAGACGCTTTGTA |
| 102 | FSV04.5 | CGGGAACTATCACCAAACAACACCCCGGAAGGAGACGAAAACGCTTTATA |
| 103 | FSV05.5 | CGGGAACTATCACCAAACAACACCCCGGGGAGGAGACAGAAACGATTTATA |
| 104 | FSV05.6 | CGGGAACTATCACCAAACAACACCCCGGGGAGGAGACAGAAACGCTTTATA |
| 105 | FSV05.8 | CGGGAACTATCACCAAACAACACCCCGGGGAGGAGACAGAGACGCTTTATA |
| 106 | FSV06.4 | CGGGAACTATCACCAAACAACACCCCGAGGAAAGAGACAGAGACGTTTTATA |
| 107 | FSSV01 | CGGGAACTATCACCAAACAACACCCCGAAACGGCAGAAGCGTTTTGTA |
| 108 | FSSV02 | CGGGAACTATCACCAAACAACACCCCGAGTAAGGAGGAAAAAGCGCTTTATA |
| 109 | FSM01D | CGGGAACTATCACCAAACAACACCCCGGGGAGGCARAAACGYTTYATA |
| 110 | FSM02.1D | CGGGAACTATCACCAAACAACACCCCGATGGAGGMAGAARCGCTTTATA |
| 111 | FSM02.2D | CGGGAACTATCACCAAACAACACCCCGRRGGAGGCAGAAACGCTTYATA |
| 112 | FSM04.3D | CGGGAACTATCACCAAACAACACCCCGGAAAAGAGGCARAAACGSTTYATA |
| 113 | FSM04.7D | CGGGAACTATCACCAAACAACACCCCGGAAAGGAGGCAGAAACGSTTTATA |
| 114 | FSM04.11D | CGGGAACTATCACCAAACAACACCCCGGGAAAGAGGCAGAARCGSTTTATA |
| 115 | FSM04.15 1D | CGGGAACTATCACCAAACAACACCCCGGGAAGGAGGCAGAARCGCTTYRTA |
| 116 | FSM04.15 2D | CGGGAACTATCACCAAACAACACCCCGGGAAGGAGGMARAARCGCTTTATA |
| 117 | FSV02.2D | CGGGAACTATCACCAAACAACACCCCGRAGAAGRCAGAAGCGCTTTATA |
| 118 | FSV02.6D | CGGGAACTATCACCAAACAACACCCCGGAGGAGACARAAGCGCTTTATA |
| 119 | FSV03.1D | CGGGAACTATCACCAAACAACACCCCGGAAGGAGACAGAARCGCTTTGTA |
| 120 | FSV04.1.1D | CGGGAACTATCACCAAACAACACCCCGGARGRAGRCAAAAACGCTTTATA |
| 121 | FSV04.1.2D | CGGGAACTATCACCAAACAACACCCCGGRAGGAGACAAAARCGCTTTATA |
| 122 | FSV04.2D | CGGGAACTATCACCAAACAACACCCCGGAAGRAGACAAAAACGCTTYDTA |
| 123 | FSV05.3D | CGGGAACTATCACCAAACAACACCCCGGGAAGGAGACAGAGRCGATTTATA |
| 124 | FSV06.1D | CGGGAACTATCACCAAACAACACCCCGAGGRAAGAGACAGAARCGCTTTATA |
| 125 | FSV06.5.1D | CGGGAACTATCACCAAACAACACCCCGRGGAAGGAGACAGAAACGCTKKATA |
| 126 | FSV06.5.2D | CGGGAACTATCACCAAACAACACCCCGAGGAVGGAGACAGAARCGCTTTATA |
| 127 | FSV06.6 1D | CGGGAACTATCACCAAACAACACCCCGAGGAMGGAGRCAGAARCGTTTTATA |
| 128 | FSV06.6 2D | CGGGAACTATCACCAAACAACACCCCGAGGAAGGAGAMARAAACGITTTRTA |
| 129 | FSV06.6 3D | CGGGAACTATCACCAAACAACACCCCGRGGAAGGAGACAGAAACGTTTYANV |
| 130 | FSV06.7D | CGGGAACTATCACCAAACAACACCCCGAGGAAGGAGACARAGACGCTTYRTA |
| 131 | FSV06.8 1D | CGGGAACTATCACCAAACAACACCCCGRRGRAGGAGACAGAGACGTTTTATA |
| 132 | FSV06.8 2D | CGGGAACTATCACCAAACAACACCCCGAGGAAGGAGACAGRGRCGTTTTATA |
| 133 | FSV06.8 3D | CGGGAACTATCACCAAACAACACCCCGAGGAAGGAGACAGAGACGTYTTRTA |

TABLE 6-continued

| SEQ ID NO | Designation | Sequence |
|---|---|---|
| | | Selection primers for Newcastle Disease Virus |
| 134 | FSSV03D | CGGGAACTATCACCAAACAACACCCCGGAGGAAGGAGAAAAAAACGHTTTATA |
| 135 | OFSM03 | CGGGAACTATCACCAAACAACACCCCGGGAGGAGACAGAAACGCTTTATA |
| 136 | OFSM04D | CGGGAACTATCACCAAACAACACCCCGGRAARGAGRCAGARACGCTTTATA |
| 137 | OFSV02D | CGGGAACTATCACCAAACAACACCCCGGAGRAGACRGAARCGCTTTATA |
| 138 | OFSV03D | CGGGAACTATCACCAAACAACACCCCGGRAGGAGACAGARACGCTTTGTA |
| 139 | OFSV04D | CGGGAACTATCACCAAACAACACCCCGGAAGGAGACRRAAACGCTTTWTA |
| 140 | OFSV05D | CGGGAACTATCACCAAACAACACCCCGGGRAGGAGACAGARACGMTTTATA |
| 141 | OFSV06D | CGGGAACTATCACCAAACAACACCCCGAGGAARGAGACAGARACGYTTTATA |
| | | Primer name for lentogenic NDV strains |
| 142 | FSL01.3 | CGGGACAACAAACCACTATCAACCCCGGAAACAGGGGCGCCTCATA |
| 143 | FSL01.4 | CGGGACAACAAACCACTATCAACCCCGGAAACAGGGGCGCCTTATA |
| 144 | FSL01.8.1D | CGGGACAACAAACCACTATCAACCCCGGAVRCAGGGGCGCCTTATA |
| 145 | FSL01.8.2D | CGGGACAACAAACCACTATCAACCCCGGAGACAGGSGCGYCTTWTA |
| 146 | FSL02.1D | CGGGACAACAAACCACTATCAACCCCGGRAAACARGGACGCCTTATA |
| 147 | FSL02.2D | CGGGACAACAAACCACTATCAACCCCGGGAARCAGGGACGCSTKATA |
| 148 | FSL03.1D | CGGGACAACAAACCACTATCAACCCCGAGRGARRCAGGGACGTCTTATA |
| 149 | FSL03.2 D | CGGGACAACAAACCACTATCAACCCCGRGGGAAACAGGRACGTCTTATA |
| 150 | FSL03.3 D | CGGGACAACAAACCACTATCAACCCCGAGGGAAACAGGGRCGTCTTMTA |
| 151 | FSSL01D | CGGGACAACAAACCACTATCAACCCCGGGCAGGRGCGTTTGGTA |
| 152 | FSSL02D | CGGGACAACAAACCACTATCAACCCCGAGAACGACAGGARCGTTTGKTA |
| 153 | FSSL03D | CGGGACAACAAACCACTATCAACCCCGGGCAGGAGCGTCTGGTR |
| 154 | FSSL04D | CGGGACAACAAACCACTATCAACCCCGAACGKCAGGAGCGYTTGGTA |
| 155 | FSSL05D | CGGGACAACAAACCACTATCAACCCCGCGGCARGAGCGTTTGGTA |
| 156 | FSSL06D | CGGGACAACAAACCACTATCAACCCCGAGWACGTCARGAGCGTTTGGTA |
| 157 | FSSL07D | CGGGACAACAAACCACTATCAACCCCGACGRCAGGAGCGKTTGGTA |
| 158 | FSSL08D | CGGGACAACAAACCACTATCAACCCCGAACRGCAGGAGCGGTTGRTA |
| 159 | FSSL09 | CGGGACAACAAACCACTATCAACCCCGAGCAGGGGCGTTTGGTA |
| 160 | FSSL010D | CGGGACAACAAACCACTATCAACCCCGAACRGCAGGAGCGDTTGATA |
| 161 | FSSL011 | CGGGACAACAAACCACTATCAACCCCGCGGCAGGATCGTTTGGTA |
| 162 | FSSL012 | CGGGACAACAAACCACTATCAACCCCGCAGACAAGCACGCCTGATA |
| 163 | FSSL013 | CGGGACAACAAACCACTATCAACCCCGAGCAGGGGCGGTTGATA |

TABLE 7

| Pre-amplification primers for Newcastle Disease Virus | | |
|---|---|---|
| Designation | SEQ ID NO | Sequence |
| P1F | 164 | TTGATGGCAGGCCTCTTGC |
| P2R | 165 | GGAGGATGTTGGCAGCATT |

TABLE 8

| Detection primers for Newcastle Disease Virus | | |
|---|---|---|
| Designation | SEQ ID NO | Sequence |
| fdHP | 60 | Fam-isoC-CGGGAACTATCACCAAACAACACCCCG |
| fdLP | 61 | CAL orange 560-isoC-CGGGACAACAAACCACTATCAACCCCG |

REFERENCES

1. Steinhauer, D. A. Role of hemagglutinin cleavage for the pathogenicity of influenza virus. *Virology* 258, 1-20 (1999).
2. Klenk, H.-D. & Garten, W. Activation of cleavage of viral spike proteins by host proteases. in *Cellular receptors for animal viruses* (ed., Wimmer, E.) pp. 241-280. (Cold Spring Harbor Laboratory Press, Plainview, N.Y., 1994).
3. Gall, A. et al. Design and validation of a microarray for detection, hemagglutinin subtyping, and pathotyping of avian influenza viruses. *J. Clin. Microbiol.* 47, 327-334 (2009).
4. Heine, H. G., Trinidad, L., Selleck, P. & Lowther, S. Rapid detection of highly pathogenic avian influenza H5N 1 virus by TaqMan reverse transcriptase-polymerase chain reaction. *Avian Dis.* 51, 370-372 (2007).
5. Hoffmann, B. et al. Rapid and highly sensitive pathotyping of avian influenza A H5N 1 virus by using real-time reverse transcription-PCR. *J. Clin. Microbiol.* 45, 600-603 (2007).
6. Yacoub, A. et al. The rapid molecular subtyping and pathotyping of avian influenza viruses. *J. Virol. Methods* 156, 157-161 (2009).
7. Slomka, M. J. et al. Identification of sensitive and specific avian influenza polymerase chain reaction methods through blind ring trials organized in the European Union. *Avian Dis.* 51, 227-234 (2007).
8. Chamberlain, J. S., Gibbs, R. A., Ranier, J. E., Nguyen, P. N. & Caskey, C. T. Deletion screening of the Duchenne muscular dystrophy locus via multiplex DNA amplification. *Nucleic Acids Res.* 16, 11141-11156 (1988).
9. Brownie, J. et al. The elimination of primer-dimer accumulation in PCR. *Nucleic Acids Res.* 25, 3235-3241 (1997).
10. Broude, N. E., Zhang, L., Woodward, K., Englert, D. & Cantor, C. R. Multiplex allele-specific target amplification based on PCR suppression. *Proc. Natl. Acad. Sci. U.S.A.* 98, 206-211 (2001).
11. Siebert, P. D., Chenchik, A., Kellogg, D. E., Lukyanov, K. A. & Lukyanov, S. A. An improved PCR method for walking in uncloned genomic DNA. *Nucleic Acids Res.* 23, 1087-1088 (1995).
12. Pemov, A., Modi, H., Chandler, D. P. & Bavykin, S. DNA analysis with multiplex microarray-enhanced PCR. *Nucleic Acids Res.* 33, e 11 (2005).
13. Han, J. et al. Simultaneous amplification and identification of 25 human papillomavirus types with Templex technology. *J. Clin. Microbiol.* 44, 4157-4162 (2006).
14. Varley, K. E. & Mitra, R. D. Nested Patch PCR enables highly multiplexed mutation discovery in candidate genes. *Genome Res.* 18, 1844-1850 (2008).
15. Schouten, J. P. et al. Relative quantification of 40 nucleic acid sequences by multiplex ligation-dependent probe amplification. *Nucleic Acids Res.* 30, e57 (2002).
16. Hardenbol, P. et al. Multiplexed genotyping with sequence-tagged molecular inversion probes. *Nat. Biotechnol.* 21, 673-678 (2003).
17. Sherrill, C. B. et al. Nucleic acid analysis using an expanded genetic alphabet to quench fluorescence. *J. Am. Chem. Soc.* 126, 4550-4556 (2004).
18. Bela, S., Kiss, I. & Viljoen, G. J. New developments in the diagnosis of avian influenza. *Rev. Sci. Tech.* 28, 233-243 (2009).
19. Zanella, A., Dall'Ara, P. & Martino, P. A. Avian influenza epidemic in Italy due to serovar H7N1. *Avian Dis.* 45, 257-261 (2001).
20. Gall, A., Hoffmann, B., Harder, T., Grund, C. & Beer, M. Universal primer set for amplification and sequencing of HAO cleavage sites of all influenza A viruses. *J. Clin. Microbiol.* 46, 2561-2567 (2008).
21. Bao, Y. et al. The influenza virus resource at the National Center for Biotechnology Information. *J. Virol.* 82, 596-601 (2008).
22. Shortreed, M. R. et al. A thermodynamic approach to designing structure-free combinatorial DNA word sets. *Nucleic Acids Res.* 33, 4965-4977 (2005).
23. Shuber, A. P., Grondin, V. J. & Klinger, K. W. A simplified procedure for developing multiplex PCRs. *Genome Res.* 5, 488-493 (1995).
24. Edgar, R. C. MUSCLE: multiple sequence alignment with high accuracy and high throughput. *Nucleic Acids Res.* 32, 1792-1797 (2004).
25. Clamp, M., Cuff, J., Searle, S. M. & Barton, G. J. The Jalview Java alignment editor. *Bioinformatics* 20, 426-427 (2004).
26. Rychlik, W., Spencer, W. J. & Rhoads, R. E. Optimization of the annealing temperature for DNA amplification in vitro. *Nucleic Acids Res.* 18, 6409-6412 (1990).

The invention claimed is:

1. A method for genotyping N loci in a target nucleic acid molecule present in a sample, wherein N is at least 1 and each locus is located in a respective genotype marker region of the nucleic acid molecule, and corresponds to two or more genotypes, the method comprising the steps of:

a) performing a pre-amplification of each genotype marker region utilizing primer-dependent enzymatic reactions, wherein the amplification is performed with a first group of amplification primer pairs consisting of a first set of one or more different forward primers and a first set of one or more different reverse primers, yielding one or more amplicons encompassing the genotype marker region(s), and wherein each amplicon contains a region with at least one nucleotide sequence that can act as a primer binding target distinct from the genotype marker region;

b) performing on the amplicon(s) from step a) a two-level nucleic acid amplification reaction utilizing primer-dependent enzymatic reactions, wherein b1) the first level is nucleic acid amplification utilizing a second group of primer pairs binding to each amplicon produced in step a), wherein said group of primer pairs consists of a second set of one or more different forward primers and a second set of one or more different reverse primers, wherein each sequence variant of each locus is targeted by at least one primer from said second sets of primers, said at least one primer forming a set of selection primers, the selection primers being bipartite having at the 3'-end a locus recognition sequence part binding to either of said N loci at the genotype marker region, and at the 5'-end an artificial one-piece tagging sequence part being genotype specific or an artificial two-piece tagging sequence part, one piece of which is genotype specific and the other one is non-genotype specific, and wherein each selection primer binding to the target locus of the genotype marker region forms a primer pair together with another primer belonging to said second sets of primers but targeting said nucleotide sequence that can act as a primer binding target of step a), and wherein each selection primer is present in a concentration of less than 100 nM, from 10 to 0.01 nM, or approximately 0.3 nM, and the other primer of said primer pair is present in a concentration of at least 100 times or between 100 and 100 000 times that of said selection primer, to yield amplicons each containing a respective one of said N loci;

b2) the second level is nucleic acid amplification utilizing a third group of primer pairs binding to each amplicon produced in step b1), wherein said group of primer pairs, present in a concentration of at least 100 times or between 100 and 100 000 times that of said selection primers in step b1), and consists of a third set of one or more different forward primers and a third set of one or more different reverse primers, wherein each tagging sequence part of each selection primer is targeted by at least one primer from said third sets of primers, said at least one primer forming a set of detection primers, and wherein each detection primer binding to the tagging sequence part forms a primer pair together with another primer belonging to said third sets of primers but targeting said nucleotide sequence that can act as a primer binding target of step a), the detection primers having:

i) a genotype-specific sequence corresponding to the artificial one-piece tagging sequence part of the selection primers, wherein each detection primer is labelled with a genotype-specific detectable label; or ii) a non-genotype specific sequence which is common to all detection primers and corresponds to the non-specific sequence of the artificial two-piece tagging sequence part of the selection primers, wherein each detection primer is optionally labelled at the 5'-end with a detectable label or a chemical moiety;

which results in detectable amplicons each containing a respective one of said N loci labelled with genotype specific tagging sequences and, optionally, genotype specific labels;

c) genotyping said N loci of the target nucleic acid molecule by c1) detecting during, or after, the amplification thereof each label comprised in each amplicon produced in step b2i), and relating the predominant amount of detected label to a specific genotype for each locus; or c2) after amplification contacting each amplicon produced in step b2ii) with a detection array of genotype specific sequences, detecting the hybridization of each amplicon to the array, and relating the detected hybridization to a specific genotype for each locus.

2. The method according to claim 1, wherein the nucleotide sequence that can act as a primer binding target of step a) belongs to a set of sequences comprising at least one or more of: having less than 100 members, less than 20 members, 1 to 5 members, or corresponds to an artificial sequence tagging part introduced in the amplicons formed in step a) by means of said first set of primers, wherein said primers are bipartite and comprise an artificial 5'-tagging sequence and a 3'-region binding to the target nucleic acid molecule, and/or corresponds to a genomic region or regions.

3. The method according to claim 1, wherein the selection and detection primers have sequences selected to minimize primer-primer interaction, or wherein the artificial tagging sequence part of said primers has self complementary ends to form base pairs of the group of less than 10 base pairs, 3-7 base pairs, or 5 base pairs.

4. The method according to claim 1, wherein said third set of primers used in step b2) binding to the at least one sequence that can act as a primer binding target of step a) is the same as said second set of primers used in step b1) binding to the at least one sequence that can act as a primer binding target of step a).

5. The method according to claim 1, wherein said second set of primers used in step b1) binding to the at least one sequence that can act as a primer binding target of step a) is the same as either first set of primers used in step a).

6. The method according to claim 1, wherein each locus corresponds to two genotypes, and optionally wherein the presence or absence of a certain locus indicates antimicrobial resistance or non-resistance, respectively, of a microorganism.

7. The method according to claim 6, wherein the two genotypes for each locus indicate high or low pathogenicity, respectively, of a microorganism whose genome contains the locus.

8. The method according to claim 6, wherein the two genotypes correspond to the presence or absence of a locus, and optionally wherein the presence or absence of a certain locus indicates antimicrobial resistance or non-resistance, respectively, of a microorganism.

9. The method according to claim 1, wherein the primer pair of step a) consists of primers comprising the primers of SEQ ID NOs: 59 and 58, the primers of SEQ ID NOs: 57 and 56, the primers of table 7 or the primers of table 4.

10. The method according to claim 1, wherein said selection primers comprise any one of SEQ ID NOs: 1 to 55or a sequence shown in table 3 or a sequence shown in table 6.

11. The method according to claim 1, wherein said detection primers comprise SEQ ID NO:s 60 and 61.

12. A kit for performing the method according to claim 1, comprising a first group of primer pairs consisting of a first set of one or more different forward primers and a first set of one or more different reverse primers for performance of the pre-amplification step a) of claim 1, a second group of primer pairs consisting of a second set of one or more different forward primers and a second set of one or more different reverse primers, one second set of which forms a set of selection primers, wherein the selection primers are bipartite and have at the 3'-end a locus recognition sequence part and at the 5'-end an artificial one-piece tagging sequence part being genotype specific or an artificial two-piece tagging sequence part, one piece thereof being genotype specific and the other one being non-genotype specific, for performance of the first level amplification of step b1) of claim 1; a third group of primer pairs consisting of a third set of one or more different forward primers and a third set of one or more different reverse primers, one third set of which forms a set of detection primers, wherein the detection primers either have a genotype-specific sequence corresponding to the artificial one-piece tagging sequence part of the selection primers or a non-genotype specific sequence common to each detection primer and corresponding to the non-specific sequence of the artificial two-piece tagging sequence part of the selection primers, for performance of the second level amplification of step b2) of claim 1, wherein the detection primers are optionally labelled at the 5' end with a label or a chemical moiety, and optionally other ingredients of a nucleic acid amplification reaction mixture.

13. The kit according to claim 12, wherein said selection and detection primers are self complementary and are selected to minimize primer-primer interaction and are selected to form base pair numbers of less than 10 base pairs, 3to 7 base pairs, or 5 base pairs.

14. The kit according to claim 12, wherein said third set of forward primers is the same as said second set of forward primers, or said third set of reverse primers is the same as said second set of reverse primers.

15. The kit according to claim 12, wherein said second set of forward primers is the same as said first set of forward primers, or said second set of reverse primers is the same as said first set of reverse primers.

16. The kit according to claim 12, wherein the first sets of primers comprise the primers of SEQ ID NOs: 59 and 58, the primers of SEQ ID NOs: 57 and 56, or of primers of table 7 or the primers of table 4.

17. The kit according to claim 12, wherein said selection primers comprise any one of SEQ ID NOs: 1 to 55 or a sequence shown in table 3 or a sequence shown in table 6.

18. The kit according to claim 12, wherein said detection primers comprise oligonucleotides of SEQ ID NO:s 60 and 61.

* * * * *

SEQUENCE LISTING

<160> NUMBER OF SEQ ID NOS: 61

<210> SEQ ID NO 1
<211> LENGTH: 53
<212> TYPE: DNA
<213> ORGANISM: Avian influenza virus

<400> SEQUENCE: 1
cgggaactat caccaaacaa caccccgcaa ggagaragaa raagaaaaaa gag 53

<210> SEQ ID NO 2
<211> LENGTH: 52
<212> TYPE: DNA
<213> ORGANISM: Avian influenza virus

<400> SEQUENCE: 2
cgggaactat caccaaacaa caccccgaag gggagagaag aagaaaaaag ag 52

<210> SEQ ID NO 3
<211> LENGTH: 53
<212> TYPE: DNA
<213> ORGANISM: Avian influenza virus

<400> SEQUENCE: 3
cgggaactat caccaaacaa caccccgccc tcaaagaaaa agaaaaacaa gag 53

<210> SEQ ID NO 4
<211> LENGTH: 53
<212> TYPE: DNA
<213> ORGANISM: Avian influenza virus

<400> SEQUENCE: 4
cgggaactat caccaaacaa caccccgcaa agagaragaa gaarraaaag arg 53

<210> SEQ ID NO 5
<211> LENGTH: 51
<212> TYPE: DNA
<213> ORGANISM: Avian influenza virus

<400> SEQUENCE: 5
cgggaactat caccaaacaa caccccgaag agaragaaga arraagcgar g 51

<210> SEQ ID NO 6
<211> LENGTH: 49
<212> TYPE: DNA
<213> ORGANISM: Avian influenza virus

<400> SEQUENCE: 6
cgggaactat caccaaacaa caccccggtc cctcaaagga agaaaagag 49

<210> SEQ ID NO 7
<211> LENGTH: 52
<212> TYPE: DNA
<213> ORGANISM: Avian influenza virus

<400> SEQUENCE: 7
cgggaactat caccaaacaa caccccggag akaraagaag aaaaaagmga gg 52

<210> SEQ ID NO 8
<211> LENGTH: 52
<212> TYPE: DNA
<213> ORGANISM: Avian influenza virus

<400> SEQUENCE: 8

-continued cgggaactat caccaaacaa caccccggag akaraagaag aaaaaagagr gg 52

<210> SEQ ID NO 9
<211> LENGTH: 53
<212> TYPE: DNA
<213> ORGANISM: Avian influenza virus

<400> SEQUENCE: 9
cgggaactat caccaaacaa caccccgrga gakaraagaa gaaaraarag agg 53

<210> SEQ ID NO 10
<211> LENGTH: 53
<212> TYPE: DNA
<213> ORGANISM: Avian influenza virus

<400> SEQUENCE: 10
cgggaactat caccaaacaa caccccgrga gakaraagaa gaaaaargar agg 53

<210> SEQ ID NO 11
<211> LENGTH: 53
<212> TYPE: DNA
<213> ORGANISM: Avian influenza virus

<400> SEQUENCE: 11
cgggaactat caccaaacaa caccccggga gagagaagaa gaaaaaagag agg 53

<210> SEQ ID NO 12
<211> LENGTH: 51
<212> TYPE: DNA
<213> ORGANISM: Avian influenza virus

<400> SEQUENCE: 12
cgggaactat caccaaacaa caccccgccc tcaaagaaga aaaaaaagag g 51

<210> SEQ ID NO 13
<211> LENGTH: 53
<212> TYPE: DNA
<213> ORGANISM: Avian influenza virus

<400> SEQUENCE: 13
cgggaactat caccaaacaa caccccgcct caaagaaraa gaaaaaarag agg 53

<210> SEQ ID NO 14
<211> LENGTH: 44
<212> TYPE: DNA
<213> ORGANISM: Avian influenza virus

<400> SEQUENCE: 14
cgggaactat caccaaacaa caccccggga tcgcgtgtga ggag 44

<210> SEQ ID NO 15
<211> LENGTH: 49
<212> TYPE: DNA
<213> ORGANISM: Avian influenza virus

<400> SEQUENCE: 15
cgggaactat caccaaacaa caccccgcca aaaaaaggaa aaaaagagg 49

<210> SEQ ID NO 16
<211> LENGTH: 43
<212> TYPE: DNA
<213> ORGANISM: Avian influenza virus

<400> SEQUENCE: 16
cgggaactat caccaaacaa caccccggat cgcgsgtgag gag 43

<210> SEQ ID NO 17
<211> LENGTH: 47
<212> TYPE: DNA
<213> ORGANISM: Avian influenza virus

<400> SEQUENCE: 17
cgggaactat caccaaacaa caccccgcca aagaggagga ggagagg 47

<210> SEQ ID NO 18
<211> LENGTH: 50
<212> TYPE: DNA
<213> ORGANISM: Avian influenza virus

<400> SEQUENCE: 18
cgggaactat caccaaacaa caccccgcca aaaaagagga aaaagagagg 50

<210> SEQ ID NO 19
<211> LENGTH: 49
<212> TYPE: DNA
<213> ORGANISM: Avian influenza virus

<400> SEQUENCE: 19
cgggaactat caccaaacaa caccccgttc caaaaaggaa aaagagagg 49

<210> SEQ ID NO 20
<211> LENGTH: 52
<212> TYPE: DNA
<213> ORGANISM: Avian influenza virus

<400> SEQUENCE: 20
cgggaactat caccaaacaa caccccgaaa ctccaaaaag aagaarmaga gg 52

<210> SEQ ID NO 21
<211> LENGTH: 53
<212> TYPE: DNA
<213> ORGANISM: Avian influenza virus

<400> SEQUENCE: 21
cgggaactat caccaaacaa caccccgcca aaaaagaaaa agaaaaagag agg 53

<210> SEQ ID NO 22
<211> LENGTH: 50
<212> TYPE: DNA
<213> ORGANISM: Avian influenza virus

<400> SEQUENCE: 22
cgggaactat caccaaacaa caccccgccc aaaaaaagaa gaaaragagg 50

<210> SEQ ID NO 23
<211> LENGTH: 53
<212> TYPE: DNA
<213> ORGANISM: Avian influenza virus

<400> SEQUENCE: 23
cgggaactat caccaaacaa caccccggaa attccaaaaa agaaaaagag agg 53

<210> SEQ ID NO 24
<211> LENGTH: 53
<212> TYPE: DNA
<213> ORGANISM: Avian influenza virus

<400> SEQUENCE: 24
cgggaactat caccaaacaa caccccgaga gagggaggaa gaagaaaaag agg 53

<210> SEQ ID NO 25
<211> LENGTH: 52
<212> TYPE: DNA
<213> ORGANISM: Avian influenza virus

<400> SEQUENCE: 25
cgggaactat caccaaacaa caccccgaaa gagagagaag gaaaaagaga gg 52

<210> SEQ ID NO 26
<211> LENGTH: 51
<212> TYPE: DNA
<213> ORGANISM: Avian influenza virus

<400> SEQUENCE: 26
cgggaactat caccaaacaa caccccgaaa aaagaaaaag aaaaagaggc c 51

<210> SEQ ID NO 27
<211> LENGTH: 48
<212> TYPE: DNA
<213> ORGANISM: Avian influenza virus

<400> SEQUENCE: 27
cgggaactat caccaaacaa caccccgccc gagaargaga aagagagg 48

<210> SEQ ID NO 28
<211> LENGTH: 51
<212> TYPE: DNA
<213> ORGANISM: Avian influenza virus

<400> SEQUENCE: 28
cgggaactat caccaaacaa caccccgttc caaaaagaga acaaaaagag g 51

<210> SEQ ID NO 29
<211> LENGTH: 52
<212> TYPE: DNA
<213> ORGANISM: Avian influenza virus

<400> SEQUENCE: 29
cgggaactat caccaaacaa caccccgaaa tcccaaagag aaagaaaaga gg 52

<210> SEQ ID NO 30
<211> LENGTH: 50
<212> TYPE: DNA
<213> ORGANISM: Avian influenza virus

<400> SEQUENCE: 30
cgggaactat caccaaacaa caccccgccc raagaagaga gagaagagag 50

<210> SEQ ID NO 31
<211> LENGTH: 45
<212> TYPE: DNA
<213> ORGANISM: Avian influenza virus

<400> SEQUENCE: 31
cgggaactat caccaaacaa caccccggcg caggcagaaa agagg 45

<210> SEQ ID NO 32
<211> LENGTH: 46
<212> TYPE: DNA

-continued

<213> ORGANISM: Avian influenza virus

<400> SEQUENCE: 32
cgggaactat caccaaacaa caccccgaca tgcgcaaaaa aagagg 46

<210> SEQ ID NO 33
<211> LENGTH: 50
<212> TYPE: DNA
<213> ORGANISM: Avian influenza virus

<400> SEQUENCE: 33
cgggacaaca aaccactatc aaccccgaty cctcararag raacaaragg 50

<210> SEQ ID NO 34
<211> LENGTH: 49
<212> TYPE: DNA
<213> ORGANISM: Avian influenza virus

<400> SEQUENCE: 34
cgggacaaca aaccactatc aaccccgtyc ctcararagr aacaaragg 49

<210> SEQ ID NO 35
<211> LENGTH: 50
<212> TYPE: DNA
<213> ORGANISM: Avian influenza virus

<400> SEQUENCE: 35
cgggacaaca aaccactatc aaccccggty cctcararag agacaaragg 50

<210> SEQ ID NO 36
<211> LENGTH: 50
<212> TYPE: DNA
<213> ORGANISM: Avian influenza virus

<400> SEQUENCE: 36
cgggacaaca aaccactatc aaccccggty cctcararag rtacaaragg 50

<210> SEQ ID NO 37
<211> LENGTH: 48
<212> TYPE: DNA
<213> ORGANISM: Avian influenza virus

<400> SEQUENCE: 37
cgggacaaca aaccactatc aaccccgccc tcagagagag acgagagg 48

<210> SEQ ID NO 38
<211> LENGTH: 48
<212> TYPE: DNA
<213> ORGANISM: Avian influenza virus

<400> SEQUENCE: 38
cgggacaaca aaccactatc aaccccgccc tcaacgagaa acaagagg 48

<210> SEQ ID NO 39
<211> LENGTH: 48
<212> TYPE: DNA
<213> ORGANISM: Avian influenza virus

<400> SEQUENCE: 39
cgggacaaca aaccactatc aaccccgycc tcaaarggag acaagagg 48

<210> SEQ ID NO 40
<211> LENGTH: 48

<212> TYPE: DNA
<213> ORGANISM: Avian influenza virus

<400> SEQUENCE: 40
cgggacaaca aaccactatc aaccccgcct gaaaytccaa aagraagg 48

<210> SEQ ID NO 41
<211> LENGTH: 50
<212> TYPE: DNA
<213> ORGANISM: Avian influenza virus

<400> SEQUENCE: 41
cgggacaaca aaccactatc aaccccgcct gaaaytccaa aaggaaaagg 50

<210> SEQ ID NO 42
<211> LENGTH: 48
<212> TYPE: DNA
<213> ORGANISM: Avian influenza virus

<400> SEQUENCE: 42
cgggacaaca aaccactatc aaccccgyga aattccaaar ggaagagg 48

<210> SEQ ID NO 43
<211> LENGTH: 47
<212> TYPE: DNA
<213> ORGANISM: Avian influenza virus

<400> SEQUENCE: 43
cgggacaaca aaccactatc aaccccgcga artyccaaar ggragag 47

<210> SEQ ID NO 44
<211> LENGTH: 47
<212> TYPE: DNA
<213> ORGANISM: Avian influenza virus

<400> SEQUENCE: 44
cgggacaaca aaccactatc aaccccggaa aycccaaakg gaagagg 47

<210> SEQ ID NO 45
<211> LENGTH: 46
<212> TYPE: DNA
<213> ORGANISM: Avian influenza virus

<400> SEQUENCE: 45
cgggacaaca aaccactatc aaccccgcyg aartcccraa kggaar 46

<210> SEQ ID NO 46
<211> LENGTH: 49
<212> TYPE: DNA
<213> ORGANISM: Avian influenza virus

<400> SEQUENCE: 46
cgggacaaca aaccactatc aaccccgcct garaytccaa aaggragag 49

<210> SEQ ID NO 47
<211> LENGTH: 48
<212> TYPE: DNA
<213> ORGANISM: Avian influenza virus

<400> SEQUENCE: 47
cgggacaaca aaccactatc aaccccgctg araytccaaa gggragag 48

<210> SEQ ID NO 48

-continued

<211> LENGTH: 49
<212> TYPE: DNA
<213> ORGANISM: Avian influenza virus

<400> SEQUENCE: 48
cgggacaaca aaccactatc aaccccgctg aaattccaaa aggaagagg 49

<210> SEQ ID NO 49
<211> LENGTH: 52
<212> TYPE: DNA
<213> ORGANISM: Avian influenza virus

<400> SEQUENCE: 49
cgggacaaca aaccactatc aaccccgaat gtycctcaaa ragaaacaag ag 52

<210> SEQ ID NO 50
<211> LENGTH: 49
<212> TYPE: DNA
<213> ORGANISM: Avian influenza virus

<400> SEQUENCE: 50
cgggacaaca aaccactatc aaccccggtt cctcaaagag acacaaggg 49

<210> SEQ ID NO 51
<211> LENGTH: 49
<212> TYPE: DNA
<213> ORGANISM: Avian influenza virus

<400> SEQUENCE: 51
cgggacaaca aaccactatc aaccccgttc cccaaagaga aaaaagagg 49

<210> SEQ ID NO 52
<211> LENGTH: 48
<212> TYPE: DNA
<213> ORGANISM: Avian influenza virus

<400> SEQUENCE: 52
cgggacaaca aaccactatc aaccccgtcc tcaaagggaa acaagagg 48

<210> SEQ ID NO 53
<211> LENGTH: 48
<212> TYPE: DNA
<213> ORGANISM: Avian influenza virus

<400> SEQUENCE: 53
cgggacaaca aaccactatc aaccccgtgg agtcccaaga aaaagagg 48

<210> SEQ ID NO 54
<211> LENGTH: 49
<212> TYPE: DNA
<213> ORGANISM: Avian influenza virus

<400> SEQUENCE: 54
cgggacaaca aaccactatc aaccccgcgg aaaatccraa gamkagagg 49

<210> SEQ ID NO 55
<211> LENGTH: 49
<212> TYPE: DNA
<213> ORGANISM: Avian influenza virus

<400> SEQUENCE: 55
cgggacaaca aaccactatc aaccccgctg aaatcccaaa gaaaagagg 49

-continued

```
<210> SEQ ID NO 56
<211> LENGTH: 21
<212> TYPE: DNA
<213> ORGANISM: Avian influenza virus

<400> SEQUENCE: 56

atgtccgaga tatgttaagc a                                                21


<210> SEQ ID NO 57
<211> LENGTH: 20
<212> TYPE: DNA
<213> ORGANISM: Avian influenza virus

<400> SEQUENCE: 57

tttgtaatct gcagcagttc                                                  20


<210> SEQ ID NO 58
<211> LENGTH: 27
<212> TYPE: DNA
<213> ORGANISM: Avian influenza virus

<400> SEQUENCE: 58

cctccagart atgcmtayaa aattgtc                                          27


<210> SEQ ID NO 59
<211> LENGTH: 23
<212> TYPE: DNA
<213> ORGANISM: Avian influenza virus

<400> SEQUENCE: 59

taccaaccgt ctaccatkcc ytg                                              23


<210> SEQ ID NO 60
<211> LENGTH: 27
<212> TYPE: DNA
<213> ORGANISM: Avian influenza virus

<400> SEQUENCE: 60

cgggaactat caccaaacaa caccccg                                          27


<210> SEQ ID NO 61
<211> LENGTH: 27
<212> TYPE: DNA
<213> ORGANISM: Avian influenza virus

<400> SEQUENCE: 61

cgggacaaca aaccactatc aaccccg                                          27
```